US006492335B1

(12) United States Patent
Lerchen et al.

(10) Patent No.: US 6,492,335 B1
(45) Date of Patent: Dec. 10, 2002

(54) GLYCOCONJUGATES FROM MODIFIED CAMPTOTHECIN DERIVATIVES (20-O-LINKAGE)

(75) Inventors: Hans-Georg Lerchen; Karsten von dem Bruch, both of Leverkusen; Jörg Buamgarten; Michael Sperzel, both of Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/269,317
(22) PCT Filed: Sep. 17, 1997
(86) PCT No.: PCT/EP97/05088
§ 371 (c)(1),
(2), (4) Date: Mar. 24, 1999
(87) PCT Pub. No.: WO98/14459
PCT Pub. Date: Apr. 9, 1998

(30) Foreign Application Priority Data

Sep. 30, 1996 (DE) ......................... 196 40 206
Oct. 23, 1996 (DE) ......................... 196 43 764

(51) Int. Cl.[7] ..................... A61K 31/70; A61K 31/675; A61K 31/44; C07F 9/06
(52) U.S. Cl. ..................... 514/25; 514/27; 514/32; 514/34; 514/81; 514/283; 546/23; 546/48
(58) Field of Search ..................... 514/25, 27, 32, 514/34, 81, 283; 546/23, 48

(56) References Cited

U.S. PATENT DOCUMENTS 4,943,579 A    7/1990   Vishnuvajjala et al. ..... 514/283

FOREIGN PATENT DOCUMENTS

| DE | 42 36 237 | * | 4/1994 |
| EP | 0 418 099 | * | 9/1990 |
| EP | 0 624 377 | * | 5/1994 |
| EP | 0 640 622 | * | 3/1995 |
| EP | 0 757 049 | * | 2/1997 |
| EP | 0 781 781 | * | 7/1997 |
| WO | 95/10304 | * | 4/1995 |
| WO | WO 96 02546 A | | 2/1996 |
| WO | 96/03152 | * | 2/1996 |
| WO | 96/26950 | * | 9/1996 |
| WO | 96/31532 | * | 10/1996 |

OTHER PUBLICATIONS

Yaegashi et al., "Chemical Modification of an Antitumor Alkaloid, 20(S)–Camptothecin: Glycosides, Phosphates and Sulfates of 7–ethyl–10–hydroxycamptothecin", Chem. Pharm. Bull., vol. 40(1): 131–135, Jan. 1992.*

Narita et al., "Inhibition of beta–glucuronidase by natural glucuronides of Kampo medicines using glucuronide of SN–38 (7–ethyl–10–hydroxycamptothecin as a substrate", Xenobiotica, vol. 23(1): 5–10, Jan. 1993.*

Takahashi et al., "The Role of Glucuronidation in 7–ethyl–10–hydroxycamptothecin Resistance in vitro", vol. 88: 1211–1217, Dec. 1997.*

Takasuna et al., "Protective Effects of Kampo Medicines and Baicalin against Intestinal Toxicity of a New Anticancer Camptothecin Derivative, Irinotecan Hydrochloride (CPT–11), in Rats", Jpn. J. Cancer Res., vol. 86: 978–984, Oct. 1995.*

Chu et al., "Multispecific Organ Anion Transporter is Responsible for the Biliary Excretion of the Camptothecin Derivative Irinotecan and its Metabolites in Rats", J. Pharm. Exp. Ther., vol. 281(1): 304–314, Jan. 1997.*

Wall et al., Journal of the American Chemical Society, 88:3888–3890, (Aug. 20, 1996).

Y.C. Lee and R.T. Lee, Lectins and Cancer, 1991, pp. 53–69, editors: Gabius H.J. and Gabius S., Springer–Verlag.

Jiang et al., Tetrahedron Lett., vol. 34, No. 42, 6705–6708, (1993).

S. Sawada, et al., Chem. Pharm. Bull. vol. 39(6) (1991) 1446–1454.

Wani et al., J. Med. Chem., vol. 29, 2358–2363, (1986).

Sawada et al, Chem. Pharm. Bull., vol. 39(10), 2574–2580, (1991).

Gupta, Elora et al: "Pharmacokinetic modulation of irinotecan and metabolites by cyclosporin A" Cancer Research (1996), 56(6), 1309–14 Coden: CNREA8; ISSN: 0008–5472, Mar. 15, 1996 XP002053618. See p. 1309, left–hand column, paragraph 2—p. 1309, right–hand column paragraph 1.

Chemical Abstracts, vol. 126, No. 4, Jan. 27, 1997, Columbus, Ohio, US; abstract No. 46340, Kitajima, Mariko, et al: "Production of camptothecinoids by utilizing cell cultures of ophiorrhiza pumila and synthetic studies of their related compounds" XP002053619 (see abstract).

Tennen Yuki Kagobutsu Toronkai Koen Yoshishu (1996), 38th, 283–288 Coden: Tykyds, Nov. 27, 1996.

\* cited by examiner

Primary Examiner—James O. Wilson
Assistant Examiner—Leigh C. Maier
(74) Attorney, Agent, or Firm—Norris McLaughlin & Marcus

(57) ABSTRACT

The present invention relates to glycoconjugates of camptothecin derivatives in which at least one carbohydrate component is linked via suitable spacers with the 20-hydroxyl group of a camptothecin derivative. The invention furthermore relates to processes for preparing the compounds according to the invention and to their use as medicaments, in particular in connection with cancer.

11 Claims, No Drawings

GLYCOCONJUGATES FROM MODIFIED CAMPTOTHECIN DERIVATIVES (20-O-LINKAGE)

This is the U.S. National Stage entry under 35 USC 371 of PCT/EP 97/05088, filed Sep. 17, 1997.

The present invention relates to glycoconjugates of camptothecin derivatives in which at least one carbohydrate component is linked via suitable spacers with the 20-hydroxyl group of a camptothecin derivative. The invention furthermore relates to processes for preparing the compounds according to the invention and to their use as medicaments, in particular in connection with cancer.

20(S)-Camptothecin is a pentacyclic alkaloid which was isolated in 1966 by Wall et al. (J.Am.Chem.Soc. 88, 3888 (1966)). It has a high antitumour activity potential in numerous in vitro and in vivo tests. Unfortunately, however, the promising potential failed to be realized in the clinic because of toxicity and solubility problems.

By opening the E ring lactone and formation of the sodium salt, a water-soluble compound was obtained which is in a pH-dependent equilibrium with the ring-closed form. Here too, clinical studies have been unsuccessful until now.

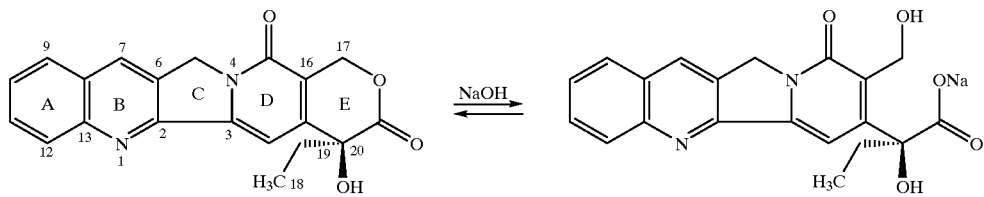

Approximately 20 years later, it was found that the biological activity is to be attributed to an enzyme inhibition of the topoisomerase I. Since then, the research activities have been increased again in order to find camptothecin derivatives which are more compatible and active in vivo.

To improve the water-solubility, salts of A ring- and B ring-modified camptothecin derivatives and of 20-O-acyl derivatives having ionizable groups have been described (Vishnuvajjala et al. U.S. Pat. No. 4,943,579). The latter prodrug concept was later also applied to modified camptothecin derivatives (Wani et al. WO 9602546). In vivo, however, the 2-O-acyl prodrugs described have a very short half-life and are very rapidly cleaved to give the parent structure.

Surprisingly, we have now found that the linkage of carbohydrate derivatives for example via peptide spacers on the 20-hydroxyl group of A- and/or B-ring-modified camptothecin derivatives leads to a class of compounds having highly interesting properties:

By means of the ester-like linkage of the carrier radicals to the 20-hydroxyl group, the lactone ring in the camptothecin derivatives, which is important for the action, is stabilized.

The conjugates obtained in this manner have high in vitro activity against tumour cell lines and tumour xenografts.

Compared with the underlying toxophores, they have markedly higher tolerability and tumour selectivity and improved solubility, in particular in aqueous media.

In vivo, they exhibit excellent therapeutic activity over several dose stages.

In extracellular medium and in blood, they are considerably more stable than the above-described 20-O-acyl prodrugs of camptothecin.

The invention relates to compounds of the general formula (I)

in which

Cp represents a group of the formulae

1)

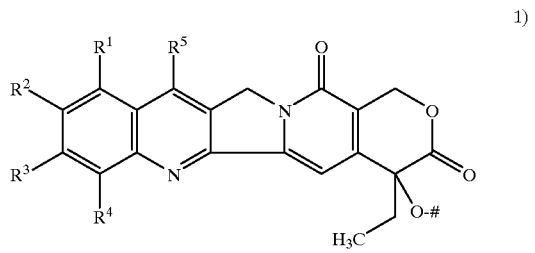

in which $R^1$, $R^2$, $R^3$ and $R^4$ independently of one another may represent hydrogen, alkyl having up to 3 carbon atoms, halogen, amino, hydroxyl or nitro or $R^2$ and $R^3$ together represent a group of the formula

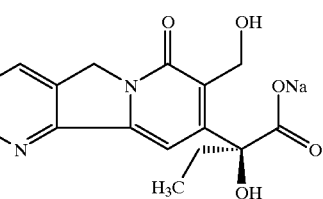

m may have the values 1 or 2 and $R^5$ represents —$CH_2$—O—*, —$CH_2$—NH*,

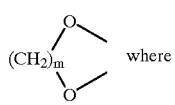

or represents

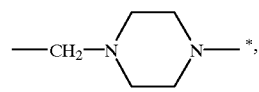

in which $R^6$ represents arylmethyl or hetarylmethyl,

2)

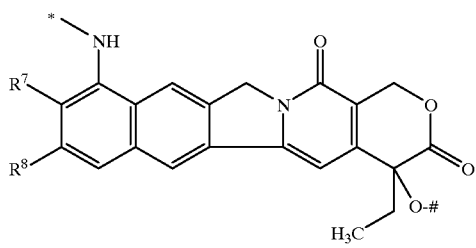

in which
$R^7$ and $R^8$ are as defined for $R^2$ and $R^3$ and may be identical or different to these,

3)

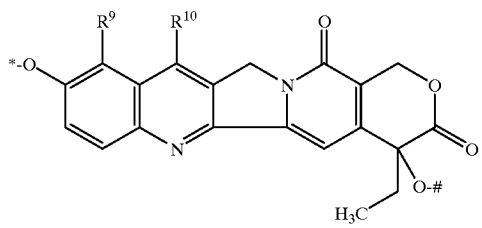

in which
$R^9$ represents hydrogen or —$CH_2$—$N(CH_3)_2$ and
$R^{10}$ represents hydrogen or ethyl, or

4)

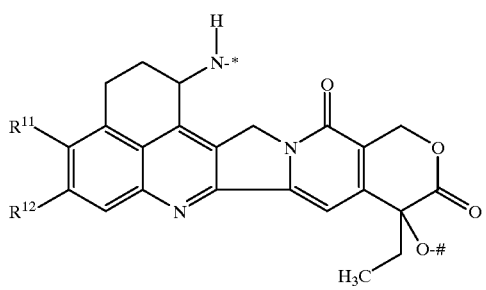

in which
$R^{11}$ and $R^{12}$ are as defined for $R^2$ and $R^3$ and may be identical or different to these, or

5)

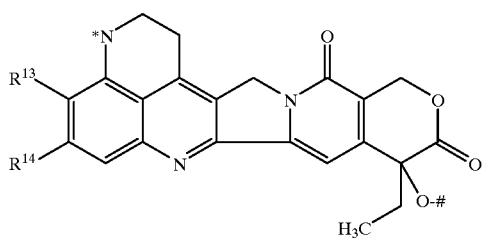

in which
$R^{13}$ and $R^{14}$ are as defined for $R^2$ and $R^3$ and may be identical or different to these, where Cp is attached to A on the positions labelled # and attached to B on the positions labelled *,
A represents a radical of the formula

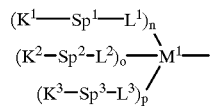

where $1 \leq (n+o+p) \leq 3$,
B represents hydrogen or a radical of the formula

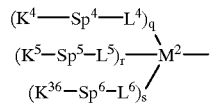

where $0 \leq (q+r+s) \leq 3$, in which
$M^1$ and $M^2$ independently of one another each represent a bridge grouping whose main chain includes up to 21 atoms in linear order,
$L^1$, $L^2$, $L^3$, $L^4$, $L^5$ and $L^6$ independently of one another each represent linker groupings customarily used in glycoconjugate chemistry, (see review article Lee Y. C. and Lee R. in Lectins and Cancer 1991, 53–69, ed. by Gabius H. J. and Gabius S., Springer-Verlag),
$Sp^1$, $Sp^2$, $Sp^3$, $Sp^4$, $Sp^5$ and $Sp^6$ independently of one another each represent arylene having up to 10 carbon atoms or represent alkylene having up to 8 carbon atoms which are in each case optionally substituted, and $K^1$, $K^2$, $K^3$, $K^4$, $K^5$ and $K^6$ independently of one another each represent a radical of the formula (II)

(II)

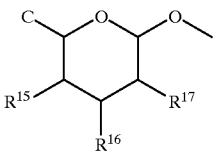

in which
C represents methyl, hydroxymethyl, alkoxymethyl having up to 6 carbon atoms, acyloxymethyl having up to 6 carbon atoms or a radical of the formula —$CH_2$—D
in which
D represents a radical of the formula (II),
$R^{15}$, $R^{16}$ and $R^{17}$ independently of one another each represent hydrogen, hydroxyl, optionally hydroxyl-substituted alkoxy having up to 6 carbon atoms, amino which is optionally substituted by alkyl or acyl having up to 6 carbon atoms, halogen, sulphate or a group of the formula

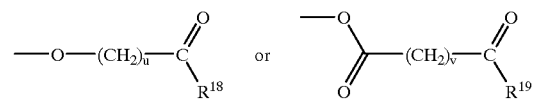

in which
$R^{18}$ and $R^{19}$ independently of one another each represent hydroxyl or alkoxy having up to 6 carbon atoms or represent amino which is optionally substituted by alkyl having up to 6 carbon atoms, and u and v independently of one another may each have the values 0, 1, 2, 3 or 4;
or
$R^{15}$, $R^{16}$ and $R^{17}$ independently of one another each represent a radical of the formula (II)
or
two of the radicals $R^{15}$, $R^{16}$, $R^{17}$ together represent an epoxy group,
or compounds of the formula:

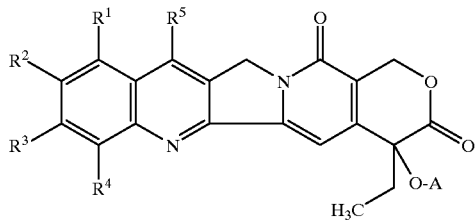

in which
$R^1$, $R^2$, $R^3$, $R^4$, and A are as defined above;
$R^5$ represents H, —CH$_2$CH$_3$,

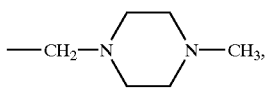

or represents —CH$_2$—N(CH$_2$CH$_3$)R$^6$,
in which $R^6$ represents arylmethyl or heterylmethyl,
and their isomers, isomer mixtures and salts.

Unless stated otherwise in the context of the invention, the term "alkyl groups" includes straight-chain, branched, cyclic and cycloalkyl-radical-containing alkyl radicals. Correspondingly, this definition also applies to all the other radicals containing alkyl groups, such as, for example, alkoxy, acyl, etc.

The terms arylmethyl and hetarylmethyl given in the definition of $R^6$ may represent, for example, phenylmethyl or pyridylmethyl.

Preference is given to compounds of the general formula (I) in which $K^1$, $K^2$, $K^3$, $K^4$, $K^5$ and $K^6$ independently of one another may each represent a radical of the formula (II) where C represents methyl, hydroxymethyl, methoxymethyl or acetoxymethyl, $R^{15}$ represents hydrogen, hydroxyl, methoxy or a group of the formula

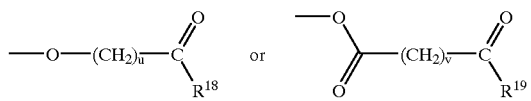

in which
u and v independently of one another may each have the values 1 or 2 and
$R^{18}$ and $R^{19}$ independently of one another each represent hydroxyl or alkoxy having up to 4 carbon atoms,
or
$R^{15}$ represents a radical of the formula (II),
$R^{16}$ represents hydrogen, hydroxyl, halogen, alkoxy having up to 4 carbon atoms, sulphate or a group of the formula

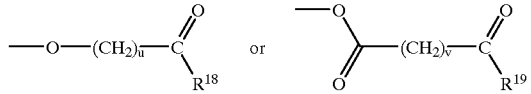

in which
u and v independently of one another may each have the values 1 or 2 and
$R^{18}$ and $R^{19}$ independently of one another each represent hydroxyl or alkoxy having up to 4 carbon atoms or represent amino which is optionally substituted by alkyl having up to 4 carbon atoms,
$R^{17}$ represents hydroxyl, alkoxy having up to 4 carbon atoms which is optionally substituted by hydroxyl, amino which is optionally substituted by alkyl or acyl having up to 4 carbon atoms, or a group of the formula

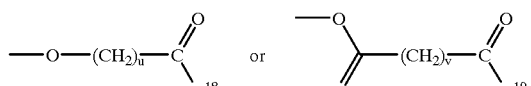

in which
u and v independently of one another may each have the values 1 or 2 and
$R^{18}$ and $R^{19}$ independently of one another each represent hydroxyl or alkoxy having up to 4 carbon atoms,
or in which
$R^{15}$ and $R^{16}$ together represent an epoxy group,
and their isomers, isomer mixtures and salts.

Very particularly preferably, $K^1$, $K^2$, $K^3$, $K^4$, $K^5$ and/or $K^6$ represent a radical of the formula (II), where C represents methyl, hydroxymethyl, methoxymethyl or acetoxymethyl, $R^{15}$ and $R^{17}$ each represent a hydroxyl group and
$R^{16}$ represents hydrogen, hydroxyl, halogen, alkoxy having up to 4 carbon atoms, sulphate or a group of the formula in which
u and v independently of one another may each have the values 1 or 2 and
$R^{18}$ and $R^{19}$ independently of one another each represent hydroxyl or alkoxy having up to 4 carbon atoms or represent amino which is optionally substituted by alkyl having up to 4 carbon atoms.

According to a particularly preferred embodiment, the carbohydrate building blocks $K^1$, $K^2$, $K^3$, $K^4$, $K^5$ and/or $K^6$ include in each case at most two monosaccharide building blocks.

Preference is furthermore given to compounds of the general formula (I) in which $Sp^1$, $Sp^2$, $Sp^3$, $Sp^4$, $Sp^5$ and/or $Sp^6$ independently of one another may each represent arylene having up to 10 carbon atoms which is attached to in each case one group $K^1$, $K^2$, $K^3$, $K^4$, $K^5$ or $K^6$ and $L^1$, $L^2$, $L^3$, $L^4$, $L^5$ or $L^6$ and which is optionally also mono- or polysubstituted by hydroxyl, carboxyl, carboxyalkyl having up to 4 carbon atoms, nitro, cyano, halogen, alkyl having up to 4 carbon atoms, halogenoalkyl having up to 4 carbon atoms or by alkoxy having up to 4 carbon atoms, and their isomers, isomer mixtures and salts.

Not taking $K^1$, $K^2$, $K^3$, $K^4$, $K^5$ or $K^6$ and $L^1$, $L^2$, $L^3$, $L^4$, $L^5$ or $L^6$ into account, $Sp^1$, $Sp^2$, $Sp^3$, $Sp^4$, $Sp^5$ and/or $Sp^6$ are particularly preferably unsubstituted or optionally substituted by halogen, nitro, alkyl having up to 6 carbon atoms, alkoxy having up to 2 carbon atoms, $-OCF_3$ and/or $CF_3$.

Very particularly preferably, $Sp^1$, $Sp^2$, $Sp^3$, $Sp^4$, $Sp^5$ and/or $Sp^6$ carry no other substituents apart from a group $K^1$, $K^2$, $K^3$, $K^4$, $K^5$ or $K^6$ and a group $L^1$, $L^2$, $L^3$, $L^4$, $L^5$ or $L^6$ each, which are attached para to one another.

Preference is furthermore given to compounds of the general formula (I) in which $L^1$, $L^2$, $L^3$, $L^4$, $L^5$ and $L^6$ independently of one another each represent

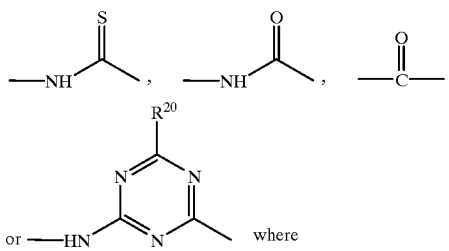

where $R^{20}$ represents chlorine or represents hydroxyalkylamino having up to 6 carbon atoms.

Particularly preferably, $L^1$, $L^2$, $L^3$, $L^4$, $L^5$ and $L^6$ each represent

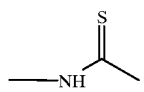

Preference is furthermore given to compounds of the general formula (I) in which $M^1$ and $M^2$ independently of one another may each represent a peptide which is attached to $L^1$, $L^2$, $L^3$, $L^4$, $L^5$ and/or $L^6$ via an amino function, is attached to Cp via an acyl function and whose amino acid building blocks may optionally carry protective groups. Particular preference is given to mono-, di- and tripeptides, in particular to mono- and dipeptides.

The amino acid building blocks are preferably selected from the group consisting of glycyl, alanyl, valyl, leucyl, lysyl, seryl, glutamyl, threonyl, asparagyl, isoleucyl, diaminopropionyl, diaminobutyryl, arginyl, histidyl and/or ornithyl.

Particular preference is given to the amino acid building blocks glycyl, alanyl, valyl, leucyl, lysyl, seryl, asparagyl, histidyl and/or glutamyl.

The compounds according to the invention may be present in stereoisomeric forms, for example as enantiomers or diastereomers, or as mixtures thereof, for example as a racemate. The invention relates both to the pure stereoisomers and to their mixtures.

If required, mixtures of stereoisomers can be separated into the stereoisomerically uniform components in a manner known per se, for example by chromatography or by crystallization processes.

The stereochemistry at the anomeric centre of the carbohydrate building blocks $K^1$, $K^2$, $K^3$, $K^4$, $K^5$ and/or $K^6$ may be α or β. Furthermore, they may be present in the D or the L form. The stereochemistry at the other centres may result in the gluco, manno, galacto, gulo, rhamno or fuco configuration.

The amino acid building blocks may in each case be present in the D or in the L form.

The camptothecin building block Cp can be present in the 20-(R) or in the 20-(S) configuration or as a mixture of these two stereoisomeric forms. Preference is given to the 20-(S) configuration.

Furthermore, owing to restricted rotation, the compounds according to the invention may occur in the form of rotational isomers or as their mixtures. The invention relates both to the pure rotational isomers and to their mixtures.

Mixtures of rotational isomers can optionally, if required, be separated into the uniform components using known methods, for example by chromatography (for example HPLC) or by crystallization processes. This can be done at the stage of the final compound and, if appropriate, also at an intermediate stage. If appropriate, the rotamerically pure end products can be prepared from rotamerically pure intermediates by conducting the synthesis in an appropriate manner.

Preferred examples of the camptothecin building block are:

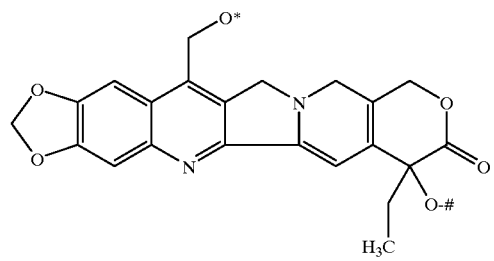

[A1]

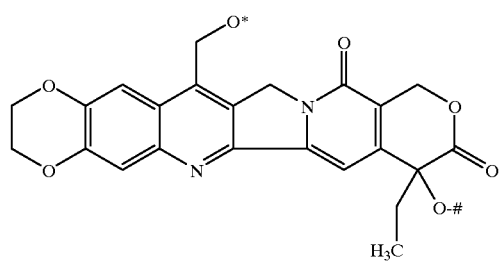

[A2]

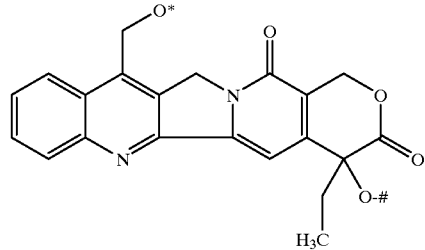

[A3]

[A4]
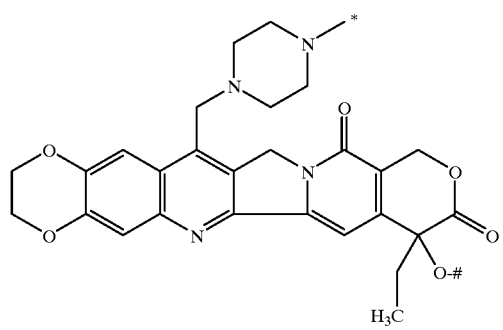
[A5]
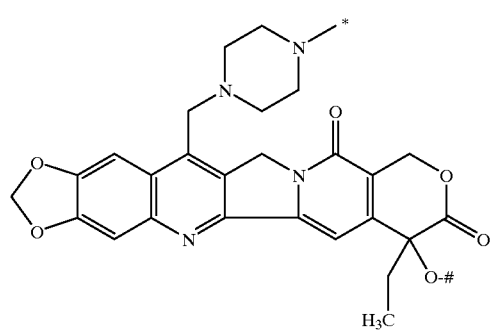
[A6]
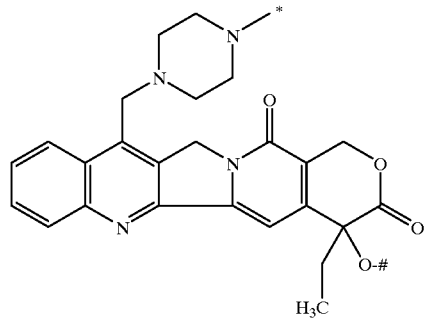
[A7]
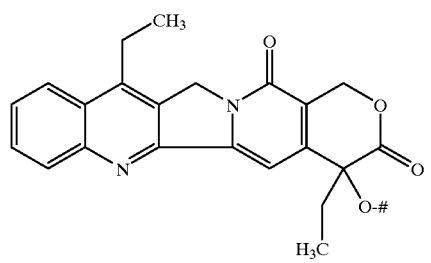
[A8]
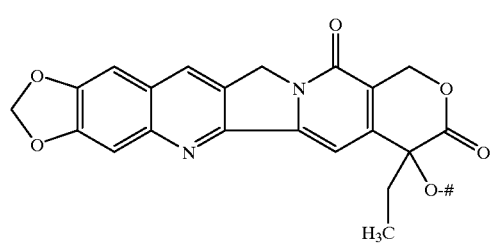
[A9]
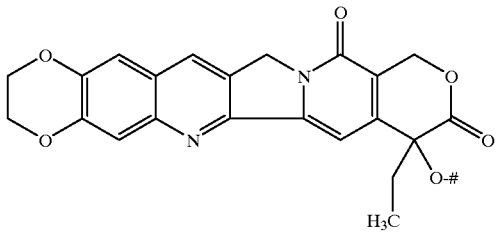
[A10]
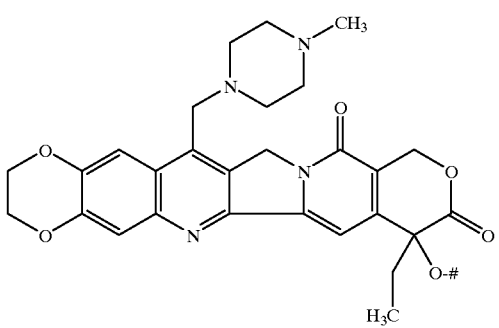
[A11]
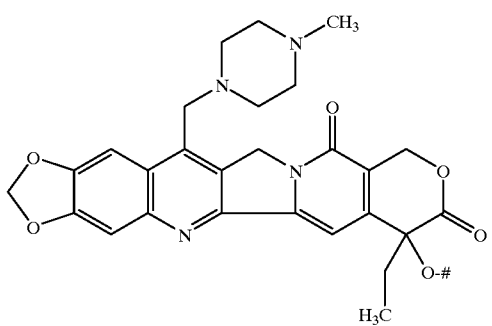
[A12]
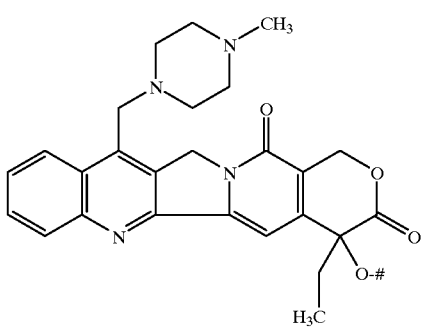
[A13]
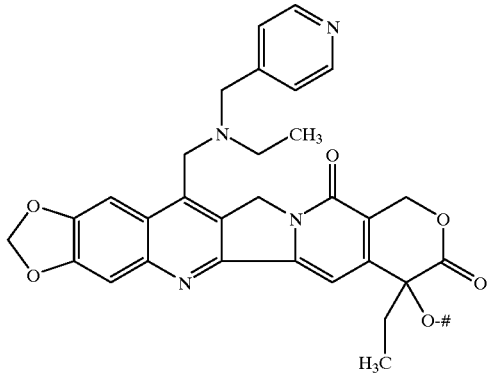

[A14]
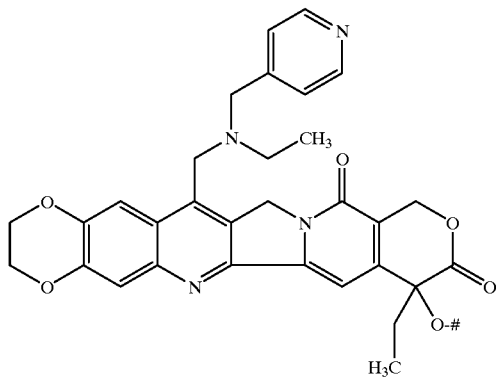

[B1]
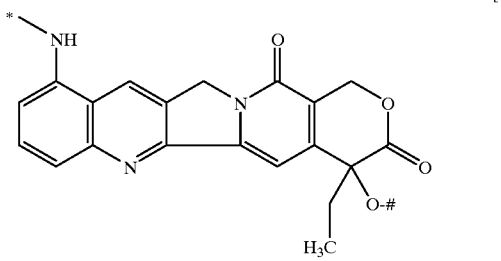

[B2]
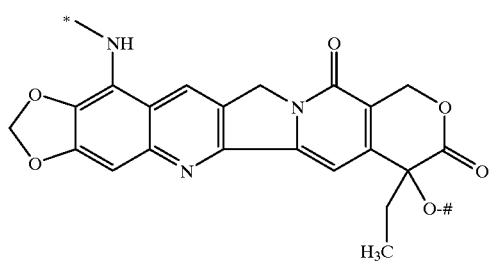

[B3]
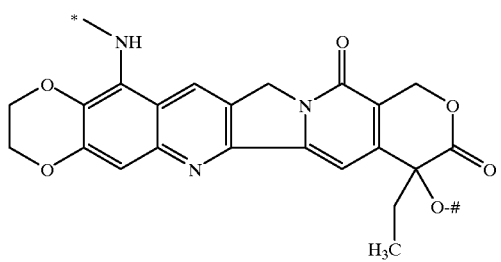

[C1]
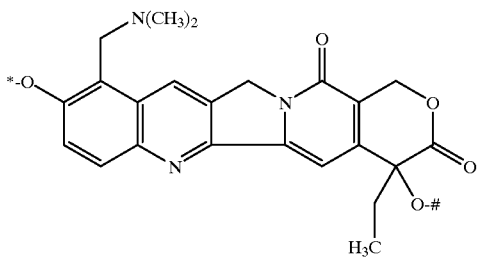

[C2]
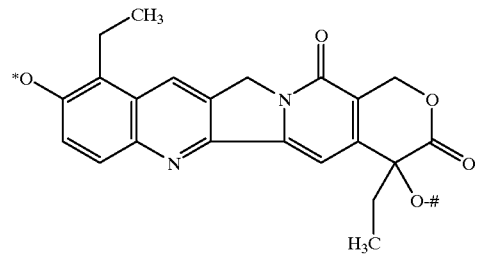

[D1]
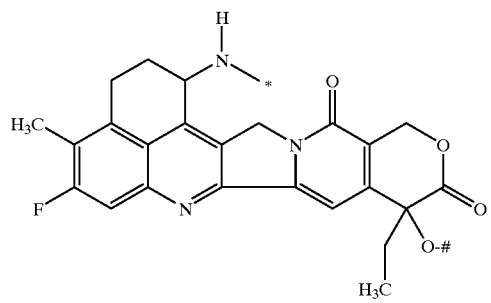

[D2]
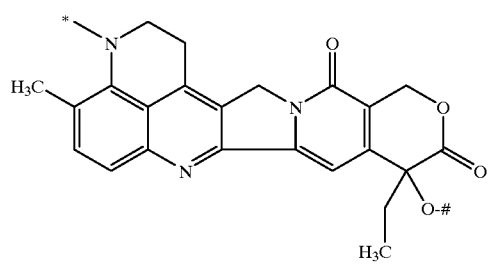

Among these examples, particular preference is given to [A3], [A7], [A8], [A9], [A10], [A11], [A14], [B1], [B2], [C2] and [D1].

By combining the preferred or particularly preferred meanings given for the individual radicals, very particularly preferred compounds of the general formula (I) result correspondingly.

The compounds according to the invention may also be present in the form of their salts. In general, salts with organic or inorganic bases or acids and also inner salts may be mentioned here.

The acids which can be adducted preferably include hydrohalic acids, such as, for example, hydrochloric acid and hydrobrornic acid, in particular hydrochloric acid, furthermore phosphoric acid, nitric acid, sulphuric acid, mono- and bifunctional carboxylic acids and hydroxycarboxylic acids, such as, for example, acetic acid, trifluoroacetic acid, maleic acid, malonic acid, oxalic acid, gluconic acid, succinic acid, fumaric acid, tartaric acid, citric acid, salicylic acid, sorbic acid and lactic acid and also sulphonic acids, such as, for example, p-toluenesulphonic acid, 1,5-naphthalenedisulphonic acid or camphorsulphonic acid.

Physiologically acceptable salts may also be the metal or ammonium salts of the compounds according to the invention which have a free carboxyl group. Particular preference is given, for example, to sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or phenethylamine.

The glycoconjugates according to the invention can be prepared, for example, by linkage of modified camptothecin derivatives with activated carboxyl components, which for their part can be moieties of protected amino acids, peptides or carbohydrate-modified peptides.

The invention thus furthermore relates to a process for preparing compounds of the general formula (I), characterized in that compounds of the general formula (III)

$$H_B—Cp—H_A \qquad (III)$$

in which Cp is as defined above and the hydrogen atoms $H_A$ and $H_B$ are located on the positions labelled # and *, respectively, are reacted, if appropriate after replacing $H_B$ by a protective group, with an activated carboxyl component $M^1a$ which corresponds to the radical $M^1$ defined above and optionally carries protective groups, in a suitable solvent, if appropriate in the presence of a base, by customary methods, one, more than one or all protective groups of $M^1$ are, if appropriate, selectively removed by known methods and the product is reacted with compounds of the general formula (IV)

$$K^1—Sp^1—L^1a \qquad (IV)$$

in which $K^1$ and $Sp^1$ are each as defined above and $L^1a$ represents a reactive precursor of the group $L^1$, where the protective groups are, if appropriate, selectively removed and various groups $K^2—Sp^2—L^2—$ and $K^3—Sp^3—L^3—$ can be introduced stepwise in a comparable manner, and that, if a carbohydrate component is to be attached to the position labelled *, the protective group which replaces $H_B$ is, if appropriate, selectively removed by known methods and the radical $M^2$ and, as desired, radicals of the formulae $K^4—Sp^4—L^4—$, $K^5—Sp^5—L^5—$ and $K^6—Sp^6—L^6—$ are introduced in the manner described above or that, if $M^1$ and/or $M^2$ are a peptide, a first amino acid radical is introduced in a comparable manner by customary methods in the form of a corresponding carboxyl component which optionally carries protective groups, protective groups are, if appropriate, removed, amino acid radicals which optionally carry protective groups are attached, protective groups are, if appropriate, removed again, the above-mentioned mentioned radicals of the formulae $K^1—Sp^1—$, $L^1—$, $K^2—Sp^2—L^2—$, $K^3—Sp^3—L^3—$, $K^4—Sp^4—L^4—$, $K^5—Sp^5—L^5—$ and/or $K^6—Sp^6—L^6—$ are introduced and, if required, protective groups are removed.

The reactions can be carried out under various pressure and temperature conditions, for example 0.5 to 2 bar, and −30 to +100° C., in suitable solvents such as dimethylformamide (DMF), tetrahydrofuran (THF), dichloromethane, chloroform, lower alcohols, acetonitrile, dioxane, water or in mixtures of the solvents mentioned. In general, reactions in DMF or THF/dichloromethane at room temperature and normal pressure are preferred.

For the activation of the carboxyl groups, possible coupling reagents are those known in peptide chemistry such as described, for example, in Jakubke/Jeschkeit: Aminosäuren, Peptide, Proteine [Amino Acids, Peptides, Proteins]; Verlag Chemie 1982 or Tetrahedr. Lett. 34, 6705 (1993). Acyl chlorides, N-carboxylic anhydrides or mixed anhydrides, for example, are preferred.

Furthermore suitable for the activation of the carboxyl groups is the formation of adducts with carbodiimides, e.g. N,N'-diethyl-, N,N'-diisopropyl-, N,N'-dicyclohexylcarbodiimide, N-(3-dimethylaminopropyl)-N'-ethyl-carbodiimide hydrochloride, N-cyclohexyl-N'-(2-morpholinoethyl)-carbodiimide metho-p-toluenesulphonate, or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluorophosphate, 1-hydroxybenzotriazole esters or hydroxysuccinimide esters. Furthermore, the amino acid components can also be employed in the form of a Leuchs' anhydride.

Bases employed can be, for example, triethylamine, ethyldiisopropylamine, pyridine, N,N-dimethylaminopyridine or others.

Protective groups employed for any other reactive functions in the camptothecin moiety or for third functions of the amino acids can be the protective groups known in peptide chemistry, for example of the urethane, alkyl, acyl, ester or amide type.

Amino protective groups in the context of the invention are the customary amino protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, tert-butoxycarbonyl (Boc), allyloxycarbonyl, vinyloxycarbonyl, 3,4,5-trimethoxybenzyloxycarbonyl, phthaloyl, 2,2,2-trichloroethoxycarbonyl, 2,2,2-trichloro-tert-butoxycarbonyl, menthyloxycarbonyl, 4-nitrophenoxycarbonyl, fluorenyl-9-methoxycarbonyl (Fmoc), formyl, acetyl, propionyl, pivaloyl, 2-chloroacetyl, 2-bromoacetyl, 2,2,2-trifluoroacetyl, 2,2,2-trichloroacetyl, benzoyl, benzyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl or 2-nitrophenylsulphenyl. The Fmoc group and the Boc group are particularly preferred.

Preferred carboxyl protective groups are linear or branched $C_1$-to $C_4$-alkyl esters.

The camptothecin derivatives linked with a bridge grouping $M^1$ and/or $M^2$ can be modified with carbohydrate radicals using various methods and linker groups. Preference is given, for example, to converting p-amino-phenyl glycosides into isothiocyanates and linkage, for example, with amino groups. Furthermore, it is also easily possible to couple carboxyalkyl or aminoalkyl glycosides with amino or carboxyl groups.

The removal of protective groups in appropriate reaction steps can be carried out, for example, by the action of acid or base, hydrogenolytically or reductively in another manner.

Biological Testing

1. Growth Inhibition Test for the Determination of the Cytotoxic Properties

The human large intestine cell lines SW 480 and HT 29 (ATCC No. CCL 228 and HBT 38) and the mouse melanoma cell line B16F10 were grown in Roux dishes in RPMI 1640 medium with addition of 10% FCS. They were then trypsinized and taken up in RPMI plus 10% FCS to a cell count of 50,000 cells/ml. 100 µl of cell suspension/well were added to a 96 microwell plate and incubated for 1 day at 37° C. in a $CO_2$ incubator. A further 100 µl of RPMI Medium and 1 µl of DMSO containing the test substances were then added. The growth was checked after day 3 and day 6. To this end, 40 µl of MTT solution (3-(4,5-dimethylthiazol-2-yl)-2,5-diphenyltetrazoline bromide) having a starting concentration of 5 mg/ml of $H_2O$ were added to each microwell. Incubation was carried out for 5 hours in a $CO_2$ incubator at 37° C. The medium was then aspirated and 100 µl of i-propanol/well were added. After shaking for 30 min with 100 µl of $H_2O$, the extinction was measured at 540 nm using a Titertek Multiscan MCC/340 (Flow).

The cytotoxic action is indicated in Table 1 as the $IC_{50}$ value in each case for the SW 480 and HT 29 and B16F10 cell lines:

TABLE 1

| Example | $IC_{50}$/nM SW 480 | $IC_{50}$/nM HT 29 | $IC_{50}$/nM B16F10 |
| --- | --- | --- | --- |
| 1.1 | 15 | 10 | 30 |
| 1.5 | 100 | 60 | 300 |
| 2.1 | 7 | 5 | 15 |
| 2.3 | 6 | 3 | 9 |
| 2.4 | 5 | 3 | 10 |
| 3.1 | 10 | 8 | 150 |
| 4.1 | 40 | 40 | 300 |
| 5.1 | 70 | 40 | 200 |
| 6.1 | 150 | 200 | 3000 |

2. Haematopoietic Activity of Glycoconjugates in Comparison with the Underlying Active Compound Materials and Methods Bone marrow cells were washed out of mice femurs. $10^5$ cells were incubated at 37° C. and 7% $CO_2$ in McCoy 5A medium (0.3% agar) together with recombinant murine GM-CSF (Genzyme; stem cell colony formation) and the substances ($10^{-4}$ to 100 µg/ml). 7 days later, the colonies (<50 cells) and clusters (17–50 cells) were counted.

Results

As shown in Tab. 2, the glycoconjugates investigated show a drastically reduced inhibition of the bone marrow stem cell proliferation compared with the underlying active compound.

TABLE 2

Inhibition of the CSF-induced proliferation of mouse bone marrow stem cells.

| Example | $IC_{50}$ [µg/ml] |
| --- | --- |
| 7-ethyl-camptothecin | $2 \times 10^{-6}$ |
| 1.1 | $2 \times 10^{-3}$ |
| 9-amino-camptothecin | $1 \times 10^{-3}$ |
| 3.1 | $2 \times 10^{-2}$ |

3. In vivo Inhibition of Tumour Growth in the Nude Mouse Model

Material

For all in vivo experiments for investigation of the inhibition of tumour growth athymic nude mice (NMRI nu/nu strain) were used. The selected large-cell lung carcinoma LXFL 529 was grown by serial passage in nude mice. The human origin of the tumour was confirmed by isoenzymatic and immunohistochemical methods.

Experimental Set-up

The tumour was implanted subcutaneously into both flanks of 6 to 8 week old nu/nu nude mice. The treatment was started, depending on the doubling time, as soon as the tumours had reached a diameter of 5–7 mm. The mice were assigned to the treatment group and the control group (5 mice per group with 8–10 assessable tumours) by randomization. The individual tumours of the control group all grew progessively.

The size of the tumours was measured in two dimensions by means of a slide gauge. The tumour volume, which correlated well with the cell count, was then used for all evaluations. The volume was calculated according to the formula "length×breadth×breadth/2" ($[a \times b^2]/2$, a and b represent two diameters at right angles).

The values of the relative tumour volume (RTV) were calculated for each individual tumour by dividing the tumour size on day X with the tumour size on day 0 (at the time of randomization). The mean values of the RTV were then used for the further evaluation.

The inhibition of the increase of the tumour volume (tumour volume of the test group/control group, T/C, in per cent) was the final measured value.

Treatment

The administration of the compounds was carried out intraperitoneally (i.p.) on day 1, 2 and 3 after randomization.

Results

Using the compound from Example 1.1, the therapeutic efficacy of the glycoconjugates according to the invention is compared with the large-cell human lung tumour xenograft LXFL 529. In the case of the maximum tolerable dose (MTD) and at ½ MTD, the therapy leads to marked tumour remission.

TABLE 3

| Therapy | Dose [mg/kg/day] | Survival time [days] | Number of tumours | Relative tumour volume on day 14 [% of day 0] | Relative body weight on day 7 [% of day 0] |
| --- | --- | --- | --- | --- | --- |
| Control group | — | >21 >21 >21 | | 692 | 102 |
| 1.1 | 12.5 (MTD) | >21 >21 >21 >21 >21 | 9 | 0.1 | 95 |
| 1.1 | 6.25 | >21 >21 >21 >21 13 | 8 | 32 | 98 |

Both in vitro and in vivo, the compounds according to the invention have a surprisingly strong antitumour activity against various tumours, in particular those of the lungs and the large intestine, in combination with a high selectivity compared to non-malignant cells.

They are therefore suitable for treating cancer, in particular cancer of the lungs and the large intestine.

The present invention includes pharmaceutical preparations which, in addition to non-toxic, inert pharmaceutically suitable excipients, contain one or more compounds according to the invention or which consist of one or more active compounds according to the invention, and processes for the production of these preparations.

The active compound(s) can optionally be present in one or more of the excipients indicated above and also in microencapsulated form.

The therapeutically active compounds should preferably be present in the abovementioned pharmaceutical preparations in a concentration of from approximately 0.1 to 99.5, preferably from approximately 0.5 to 95, % by weight of the total mixture.

Apart from the compounds according to the invention, the abovementioned pharmaceutical preparations can also contain further pharmaceutically active compounds.

In general, it is proven advantageous both in human and in veterinary medicine to administer the active compound(s) according to the invention in total amounts of from approximately 0.5 to approximately 500, preferably 5 to 100, mg/kg of body weight every 24 hours, if appropriate in the form of several individual doses, to achieve the desired results. An individual dose contains the active compound(s) according to the invention preferably in amounts of from approximately 1 to approximately 80, in particular 3 to 30, mg/kg of body weight.

EXAMPLES

Carbohydrate Starting Materials

Example I.1 p-Aminophenyl 3-O-methyl-β-L-fucopyranoside

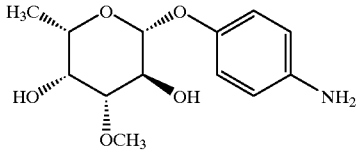

I.1.a) p-Nitrophenyl 3-O-methyl-β-L-fucopyranoside 6 g (21 mmol) of p-nitrophenyl β-L-fucopyranoside in 300 ml of absol. methanol are treated with 7.84 g (31.5 mmol) of dibutyl tin oxide and heated under reflux for 2 h. The mixture is then concentrated, and the residue is dried and then taken up in 300 ml of DMF. After addition of 15.7 ml of methyl iodide, the batch is stirred at 70° C. for 40 h. The solvent is removed under reduced pressure and the residue is taken up in 300 ml of dichloromethane. The suspension is filtered, and the solution that remains is concentrated again and subjected to flash chromatography (dichloromethane/methanol 99:1). The concentration gives 3.82 g (61%) of the target product.

I.1) p-Aminophenyl 3-O-methyl-β-L-fucopyranoside 3.81 g (12.73 mmol) of p-nitrophenyl 3-O-methyl-β-L-fucopyranoside are dissolved in methanol and, after addition of platinum dioxide, hydrogenated in a hydrogen atmosphere at a slight overpressure. After filtering off the catalyst and precipitating with ether, 3 g (88%) of the target product are obtained. [TLC: dichloromethane/methanol 9:1 $R_f$=0.53].

Example I.2 p-Aminophenyl 3-O-carboxymethyl-β-L-fucopyranoside

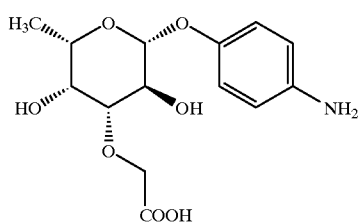

I.2.a) p-Nitrophenyl 3-O-methoxycarbonylmethyl-β-L-fucopyranoside 1 g (3.5 mmol) of p-nitrophenyl β-L-fucopyranoside and 1.3 g (5.2 mmol) of dibutyl tin oxide in 50 ml of methanol are heated under reflux for 2 h. The solution is concentrated, the residue is taken up in 50 ml of dioxane, admixed with 2 ml of methyl bromoacetate and 100 mg of tetrabutylammonium iodide, and the mixture is heated under reflux for 16 h. The solvent is evaporated off and the product is purified by flash chromatography (dichloromethane/methanol 99:1). After concentrating the appropriate fractions and precipitating from methanol/ether, 455 mg (37%) of the target compound are obtained.

I.2) p-Aminophenyl 3-O-carboxymethyl-β-L-fucopyranoside 282 mg (0.79 mmol) of p-nitrophenyl 3-methoxycarbonylmethyl-β-L-fucopyranoside are dissolved in 20 ml of methanol and admixed with 440 μl of an aqueous 2N lithium hydroxide solution. The mixture is stirred at room temperature for 2 h and then adjusted to pH 3 using acidic ion exchanger SC108 and filtered. 250 mg of palladium on activated carbon are added to the filtrate. The mixture is subsequently hydrogenated for 1.5 h using a slight hydrogen overpressure, and the catalyst is separated off and washed with methanol. Concentration, taking up in water and freeze drying gives the target product (212 mg) in 86% yield. [TLC: acetonitrile/water/glacial acetic acid 5:1:0.2 $R_f$=0.24]

The following derivatives, for example, can be used as further carbohydrate building blocks:
p-aminophenyl β-L-fucopyranoside
p-aminophenyl 2-O-methyl-β-L-fucopyranoside
p-aminophenyl 2-O-hydroxyethyl-β-L-fucopyranoside
p-aminophenyl 4-O-methyl-β-L-fucopyranoside
p-aminophenyl 3-O-methyl-α-L-fucopyranoside
p-aminophenyl 3-O-n-propyl-β-L-fucopyranoside
p-aminophenyl 3-deoxy-β-L-fucopyranoside
p-aminophenyl 3,4-dideoxy-β-L-fucopyranoside
p-aminophenyl 3,4-epoxy-β-L-fucopyranoside p-aminophenyl 4-deoxy-β-L-fucopyranoside
p-aminophenyl 3-O-methoxycarbonylmethyl-β-L-fucopyranoside
p-aninophenyl 3-O-hydroxyethyl-β-L-fucopyranoside
p-aminophenyl 2-O-carboxymethyl-β-L-fucopyranoside
p-aminophenyl 3-O-succinyl-β-L-fucopyranoside
p-aminophenyl 3,4-di-O-methyl-β-L-fucopyranoside
p-aninophenyl 3-O-carbamoylmethyl-β-L-fucopyranoside
p-aminophenyl α-L-rhamnopyranoside
p-aminophenyl β-D-galactopyranoside
p-aminophenyl 2-O-methyl-β-D-galactopyranoside
p-aminophenyl 3-O-methyl-β-D-galactopyranoside
p-aminophenyl 4-O-methyl-β-D-galactopyranoside
p-aminophenyl 6-O-methyl-β-D-galactopyranoside
p-aminophenyl 2,3-di-O-methyl-β-D-galactopyranoside
p-aminophenyl 2,4-di-O-methyl-β-D-galactopyranoside
p-aminophenyl 2,6-di-O-methyl-β-D-galactopyranoside
p-amninophenyl 3,4-di-O-methyl-β-D-galactopyranoside, acetate
p-aminophenyl 3,6-di-O-methyl-β-D-galactopyranoside
p-aminophenyl 4,6-di-O-methyl-β-D-galactopyranoside
p-aminophenyl 2,3,4-tri-O-methyl-β-D-galactopyranoside
p-aminophenyl 2,3,6-tri-O-methyl-β-D-galactopyranoside
p-aminophenyl 2,4,6tri-O-methyl-β-D-galactopyranoside
p-aminophenyl 3,4,6-tri-O-methyl-β-D-galactopyranoside
p-aminophenyl 3-deoxy-β-D-galactopyranoside
p-aminophenyl 3,4-dideoxy-β-D-galactopyranoside
p-aminophenyl 6-O-acetyl-β-D-galactopyranoside
p-aminophenyl 3-O-methoxycarbonylmethyl-β-D-galactopyranoside
p-aminophenyl 3-O-carboxymethyl-β-D-galactopyranoside, sodium salt
p-aminophenyl 3-O-carbamoylmethyl-β-D-galactopyranoside
p-aminophenyl 3-O-(N-methyl-carbamoylmethyl)-β-D-galactopyranoside
p-aminophenyl α-D-mannopyranoside
p-aminophenyl 3-O-methyl-α-D-mannopyranoside
p-aminophenyl 2,3-di-O-methyl-α-D-mannopyranoside
p-aminophenyl 3-O-methoxycarbonylmethyl-α-D-mannopyranoside
p-aminophenyl 3-O-carboxymethyl-α-D-mannopyranoside
p-aminophenyl 3-O-carbamoylmethyl-α-D-mannopyranoside
p-aminophenyl 4-O-(β-D-galactopyranosyl)-β-D-glucopyranoside
p-aminophenyl 4-O-(3'-sulphate-β-D-galactopyranosyl)-β-D-glucopyranoside, sodium salt
p-aminophenyl 4-O-(3'-O-methyl-β-D-galactopyranosyl)-β-D-glucopyranoside
p-aminophenyl 2-O-methyl-4-O-(3'-O-methyl-β-D-galactopyranosyl)-β-D-glucopyranoside
p-aminophenyl 4-O-(3',4'-di-O-methyl-β-D-galactopyranosyl)-β-D-glucopyranoside The synthesis of the following carbohydrate building blocks has already been described in EP 501 250:
Carboxymethyl β-L-fucopyranoside
5-Carboxypentyl β-L-fucopyranoside These two building blocks can be linked with peptide conjugates in the manner described in EP 501 250.

Glycoconjugates

Example 1.1

20(S)-7-Ethyl-20-O-{N$^\alpha$, N$^\epsilon$-bis-[O-(3-O-methyl-β-L-fucopyranosyl)-4-hydroxy-phenylamino-thiocarbony]-lysyl-alanyl}-camptothecin

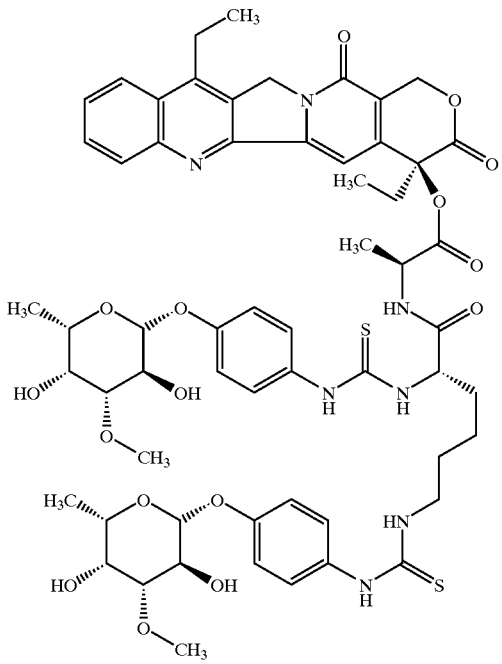

1.1.a) 20(S)-7-Ethyl-20-O-[N-(tert-butoxycarbonyl)-alanyl]-camptothecin

A solution of 1.88 g (5.0 mmol) of 20(S)-7-ethyl-camptothecin (S. Sawada et al., Chem.Pharm.Bull., 39 (1991) 1446–1454) in 100 ml of absolute dimethylformamide is admixed with stirring with 2.15 g (10.0 mmol) of N-(tert-butoxycarbonyl)-alanine-N-carboxylic anhydride and 150 mg (1.2 mmol) of 4-(N,N-dimethylamino)-pyridine. After 3 h at room temperature, a further 2.15 g (10.0 mmol) of N-(tert-butoxy-carbonyl)-alanine-N-carboxylic anhydride and 150 mg (1.2 mmol) of 4-(N,N-di-methylamino)-pyridine are added, and the mixture is stirred at room temperature overnight. The mixture is subsequently concentrated under reduced pressure and the residue is purified by flash chromatography [petroleum ether/ethyl acetate 2:1→1:1 →ethyl acetate]. This gives colourless crystals (2.02 g, 73.8%); TLC [ethyl acetate]: R$_f$=0.56; m.p.= 206–212° C.; FAB-MS: m/z=548 (M+H$^+$).

1.1.b) 20(S)-20-O-Alanyl-7-ethyl-camptothecin, trifluoroacetate

A solution of compound 1.1.a (1.81 g, 3.3 mmol) in a mixture of 70 ml of dichloromethane and 7 ml of anhydrous trifluoroacetic acid is stirred at room temperature for 90 min. Under reduced pressure, the mixture is concentrated to a small volume and the product is then precipitated with diethyl ether and washed thoroughly with diethyl ether. The product is obtained as light-yellow crystals (1.34 g, 72.3%); TLC [ethyl acetate]: R$_f$=0.05; m.p.=242° C. (Decomp.).

1.1.c) 20(S)-7-Ethyl-20-O-[N$^\alpha$,N$^\epsilon$-di-(tert-butoxycarbonyl)-lysyl-alanyl]-camptothecin 1.57 g (4.55 mmol) of N,N-di-(tert-butoxycarbonyl)-lysine and 923 mg (6.83 mmol) of 1-hydroxy-1H- benzotriazole hydrate are dissolved in 35 ml of dimethylformamide. After addition of 1.09 g (5.7 mmol) of N-ethyl-N'-(dimethylaminopropyl)-carbodiimide hydrochloride and 990 μl (5.7 mmol) of ethyl diisopropylamine, the mixture is stirred at room temperature for 30 min. A solution of compound 1.1.b (1.3 g, 2.32 mmol) in 35 ml of dimethylformamide and 408 μl (2.32 mmol) of ethyl diisopropylamine is subsequently added, and the batch is stirred at room temperature for a further 16 h. Concentration under reduced pressure and purification by flash chromatography [petroleum ether/ethyl acetate 2:1→1:1→ethyl acetate] gives light-yellow crystals (1.38 g, 75.3%); TLC [ethyl acetate]: $R_f$=0.53; m.p.=125° C. (Decomp.).

1.1.d) 20(S)-7-Ethyl-20-O-(lysyl-alanyl)-camptothecin, di-trifluoroacetate

A suspension of the above compound (1.18 g, 1.5 mmol) in dichloromethane (50 ml) is admixed with anhydrous trifluoroacetic acid (5 ml), and the resulting solution is stirred at room temperature for 1 h. After concentration under reduced pressure to a small volume, the product is precipitated out by addition of diethyl ether. The precipitate is filtered off and recrystallized from ethyl acetate. This gives yellow crystals (862 mg, 71.5%); TLC [ethyl acetate]: $R_f$=0.05; m.p.=137° C. (Decomp.).

1.1) 20(S)-7-Ethyl-20-O-{$N^\alpha$, $N^\epsilon$-bis-[O-(3-O-methyl-β-L-fucopyranosyl)-4-hydroxy-phenylamino-thiocarbonyl]-lysyl-alanyl}-camptothecin A solution of 269.4 mg (1.0 mmol) of p-aminophenyl-3-O-methyl-β-L-fucopyrano-side (Example I.1) in dioxane/water 1:1 (10 ml) is admixed with stirring with thiophosgene (150 μl, 2.0 mmol). After 10 min, the mixture is admixed with 4 equivalents of ethyldiisopropylamine and subsequently concentrated under reduced pressure, and the residue is dried under oil pump vacuum for 1 h. The resulting isothiocyanate is dissolved in 50 ml of absolute dimethylformamide and admixed with 361.7 mg (0.45 mmol) of compound 1.1.d and 317 μl (1.8 mmol) of ethyl-diisopropylamine. The mixture is stirred at room temperature for 16 h and then concentrated under reduced pressure, and the residue is purified by flash chromatography [acetonitrile/water 15:1→10:1→5:1]. The product is reprecipitated from dichloromethane/methanol using diethyl ether. This gives 203.3 mg (37.7%) of the target product as yellow crystals; m.p.=196–198° C. (Decomp.).

Example 1.2

20(S)-7-Ethyl-20-O-{$N^\alpha$, $N^\epsilon$-bis-[O-(3-O-carboxymethyl-β-L-fucopyranosyl)-4-hydroxy-phenylamino-thiocarbonyl]-lysyl-alanyl}-camptothecin, disodium salt By the method of Example 1.1, the glycoconjugate is prepared from 361.7 mg (0.45 mmol) of peptide conjugate 1.1.d and 313.3 mg (1.0 mmol) of p-aminophenyl-3-O-carboxymethyl-β-L-fucopyranoside (Example I.2).

Purification by flash chromatography [acetonitrile/water 10:1→5:1]. Conversion into the di-sodium salt using 2 equivalents of a 0.1 N aqueous sodium hydroxide solution. This gives a yellow amorphous solid (162.8 mg, 27.2%); TLC [acetonitrile/water 5:1]: $R_f$=0.09.

Example 1.3

20(S)-7-Ethyl-20-O-{$N^\alpha$-[O-(3-O-carboxymethyl-β-L-fucopyranosyl)4-hydroxy-phenylamino-thiocarbonyl]-lysyl-alanyl}-camptothecin, hydrochloride

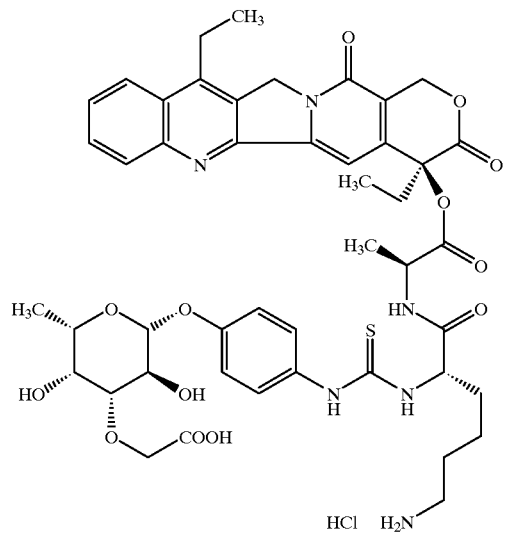

1.3.a) 20(S)-7-Ethyl-20-O-[$N^\epsilon$-(fluorenyl-9-methoxycarbonyl)-lysyl-alanyl]-camptothecin, trifluoroacetate By the method of the procedure of Example 1.1.c, the conjugate from Example 1.1.b is linked to $N^\alpha$-(tert-butoxycarbonyl)-$N^\epsilon$-(fluorenyl-9-methoxycarbonyl)-lysine and subsequently deblocked at the α-amino function according to Example 1.1.d.

1.3.b) 20(S)-7-Ethyl-20-O-{$N^\alpha$-[O-(3-O-carboxymethyl-β-L-fucopyranosyl)-4-hydroxy-phenylamino-thiocarbonyl]-$N^\epsilon$-[fluorenyl-9-methoxycarbonyl]-lysyl-alanyl}-camptothecin By the method of Example 1.1, the compound from Example 1.3.a is reacted with 1.2 equivalents of the carbohydrate derivative from Example I.2.

1.3) 20(S)-7-Ethyl-20-O-{$N^\alpha$-[O-(3-O-carboxymethyl-β-L-fucopyranosyl)-4-hydroxy-phenylamino-thiocarbonyl]-lysyl-alanyl}-camptothecin, hydrochloride The conjugate 1.3.b is deblocked using piperidine in DMF. After 30 min, the mixture is concentrated and the residue is digested twice with dichloromethane. The residue is then taken up in DMF and precipitated with methanol/ether. The product is filtered off with suction, washed with ether and then lyophilized from dioxane/water. The lyophilizate is subsequently again taken up in water, admixed with 1 equivalent of a 0.01 N HCl solution and once more lyophilized.

Example 1.4

20(S)-7-Ethyl-20-O-{$N^\alpha$-[O-(3-O-carboxymethyl-β-L-fucopyranosyl)-4-hydroxy-phenylamino-thiocarbonyl]-lysyl-valyl}-camptothecin, hydrochloride The compound is prepared by the method of Example 1.3.

Example 1.5

7-Ethyl-20-O-{N$^\alpha$-[O-(3-O-methyl-β-L-fucopyranosyl)-4-hydroxyl-phenyl-amino-thiocarbonyl]-lysyl-valyl}-camptothecin, hydrochloride

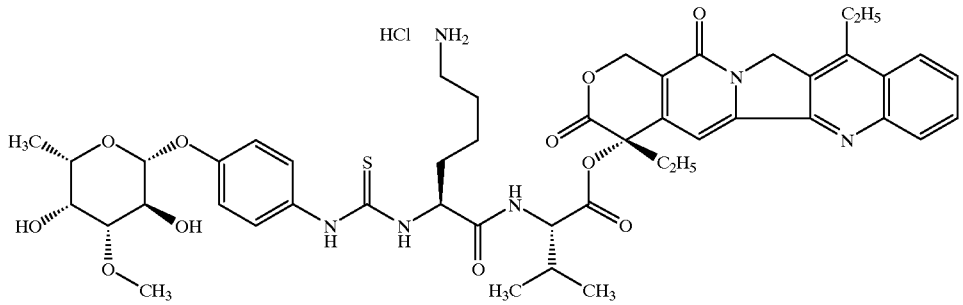

1.5.a) 20-O-[N-(tert-Butoxycarbonyl)-valyl]-7-ethyl-camptothecin

Using the process described in 1.1.a, the compound is prepared from 1.88 g (5.0 mmol) of 20(S)-7-ethyl-camptothecin (S. Sawada et al., Chem. Pharm. Bull. 39 (1991) 1446–1454) and 2.43 g (10.0 mmol) of N-(tert-butoxycarbonyl)-valine-N-carboxylic anhydride. This gives 1.46 g (51%) of beige crystals [TLC (acetonitrile): R$_f$=0.86; m.p.=224–227° C. (Decomp.); FAB-MS: m/z=576 (M+H$^+$)].

1.5.b) 7-Ethyl-20-O-valyl-camptothecin, trifluoroacetate

From compound 1.5.a (1.44 g, 2.5 mmol), the N-(tert-butoxycarbonyl) group is cleaved off as described under 1.1.b. This gives 626 mg (43%) of yellow crystals [TLC (acetonitrile): R$_f$=0.45; m.p.=160° C. (Decomp.)].

1.5.c) 20-O-[N$^\alpha$-(tert-Butoxycarbonyl)-N$^\epsilon$-(fluorenyl-9-methoxycarbonyl)-lysyl-valyl]-7-ethyl-camptothecin By the method of Example 1.1.c, 797 mg (1.7 mmol) of N$^\alpha$-(tert-butoxycarbonyl)-N$^\epsilon$-(fluorenyl-9-methoxycarbonyl)-lysine are reacted with compound 1.5.b (590 mg, 1.0 mmol). Concentration under reduced pressure and purification by flash chromatography [petroleum ether/ethyl acetate 1:2] gives beige crystals. Yield: 287 mg (31%) [TLC (ethyl acetate): R$_f$=0.50; m.p.=172° C. (Decomp.)].

1.5.d) 7-Ethyl-20-O-[N$^\epsilon$-(fluorenyl-9-methoxycarbonyl)-lysyl-valyl]-camptothecin, trifluoroacetate:

The above compound (277.8 mg, 0.3 mmol) is deprotected as described, using trifluoroacetic acid in dichloromethane. This gives 209 mg (74%) of yellow crystals [TLC (ethyl acetate): R$_f$=0.06; m.p.=199° C. (Decomp.)].

1.5.e) 20(S)-7-Ethyl-20-O-{N$^\alpha$-(O-(3-O-methyl-β-L-fucopyranosyl)-4-hydroxy-phenylamino-thiocarbonyl]-N$^\epsilon$-[fluorenyl-9-methoxy-carbonyl]-lysyl-valyl}-camptothecin By the method of Example 1.1, the compound from Example 1.5.d is reacted with 1.2 equivalents of the carbohydrate derivative from Example I.1, and the product is purified by precipitation from dichloromethane/methanol 1:1 using diethyl ether. This gives beige crystals in 35% yield [TLC (acetonitrile/ethyl acetate 1:1): R$_f$=0.68].

1.5) 20(S)-7-Ethyl-20-O-{N$^\alpha$-[O-(3-O-methyl-β-L-fucopyranosyl)4-hydroxy-phenylamino-thiocarbonyl-]-lysyl-valyl}-camptothecin, hydrochloride The conjugate 1.5.e is deblocked using piperidine in DMF. After 3 h, the mixture is concentrated and the residue is precipitated twice from dichloromethane/methanol 1:1 using diethyl ether. The product is subsequently taken up in water, admixed with 1 equivalent of a 0.01 N HCl solution and lyophilized.

Example 2.1

20(R,S)-10,11-Methylenedioxy-20-O-{N$^\alpha$,N$^\epsilon$-bis-[O-(3-O-methyl-β-L-fucopyranosyl)-4-hydroxy-phenylamino-thiocarbonyl]-lysyl-alanyl}-camptothecin

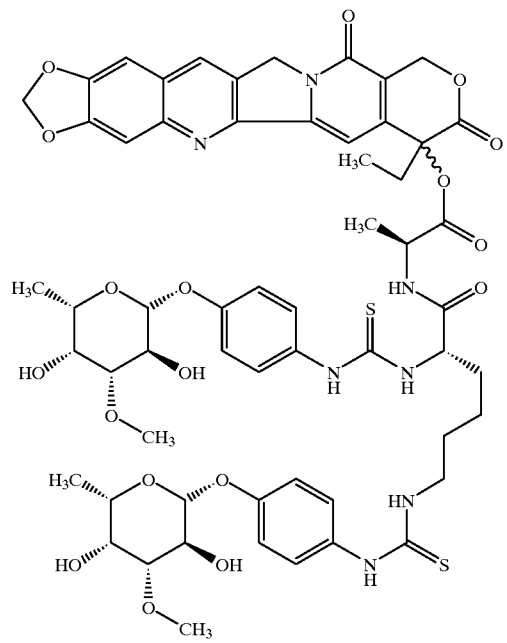

2.1.a) 20(R,S)-10,11-Methylenedioxy-camptothecin

This camptothecin derivative is prepared according to Wall et. al. (J.Med.Chem., 29 (1986), 2358) from the racemic tricycle.

2.1.b) 20(R,S)-10,11-Methylenedioxy-20-O-alanyl-camptothecin, trifluoroacetate

With stirring, a solution of 300 mg (0.765 mmol) of 20(R,S)-10,11-methylenedioxy-camptothecin in 30 ml of absolute dimethylformamide is admixed with 330 mg (1.53 mmol) of N-(tert-butoxycarbonyl)-alanine-N-carboxylic anhydride and 30 mg of 4-(N,N-dimethylamino)-pyridine. After 24 h of stirring at room temperature, in each case two more equivalents of N-(tert-butoxycarbonyl)-alanine-N-carboxylic anhydride and 30 mg of 4-(N,N-dimethylamino)-pyridine are added. After the reaction has ended, the mixture is concentrated under reduced pressure. Precipitation from dichloromethane using ether gives the protected intermediate in a yield of 80%. [TLC: dichloromethane/methanol 95:5 $R_f$=0.38]. The intermediate is taken up in 10 ml of dichloromethane and, at 0° C., 2 ml of anhydrous trifluoroacetic acid are added. After 15 min, the mixture is concentrated and the product is precipitated from dichloromethanelmethanol using ether.

Yield: 97% [FAB-MS: m/z=464=M+H].

2.1) 20(R,S)-10,11-Methylenedioxy-20-O-{$N^\alpha$, $N^\epsilon$-bis-[O-(3-O-methyl-β-L-fucopyranosyl)-4-hydroxy-phenylamino-thiocarbonyl]-lysyl-alanyl}-camptothecin By the methods of the procedures for 1.1.c, 1.1.d and 1.1, the glycoconjugate is prepared from the alanyl conjugate from Example 2.1.b.

Yield: 87% [TLC: acetonitrile/water 10:1 $R_f$=0.33] [FAB-MS: m/z=1214=M+H].

Example 2.2

20(S)-10,11-Methylenedioxy-20-O-{$N^\alpha$,$N^\epsilon$-bis-[O-(3-O-methyl-β-L-fucopyranosyl)-4-hydroxy-phenylamino-thiocarbonyl]-lysyl-alanyl}-camptothecin 2.2.a) 20(S)-10,11-Methylenedioxy-camptothecin This camptothecin derivative is prepared according to Wall et al. (J.Med.Chem., 29 (1986), 2358) from the S-configured, enantiomerically pure tricycle which can be obtained by resolution of the racemate.

2.2) 20(S)-10,11-Methylenedioxy-20-O-{$N^\alpha$,$N^\epsilon$-bis-[O-(3-O-methyl-β-L-fucopyranosyl)-4-hydroxy-phenylamino-thiocarbonyl]-lysyl-alanyl}-camptothecin Preparation by the method of Example 2.1.

Example 2.3

20(S)-10,11-Methylenedioxy-20-O-{$N^\alpha$-[O-(3-O-carboxymethyl-β-L-fucopyranosyl)-4-hydroxy-phenylamino-thiocarbonyl]-lysyl-alanyl}-camptothecin, hydrochloride 2.3.a) 20(S)-10,11-Methylenedioxy-20-O-alanyl-camptothecin, trifluoroacetate This conjugate is prepared from the compound 2.2.a by the method of 2.1.b. Yield: 72% over 2 steps [FAB-MS: m/z=464=M+H].

2.3.b) 20(S)-10,11-Methylenedioxy-20-O-{$N^\epsilon$-[fluorenyl-9-methoxycarbonyl]-lysyl-alanyl}-camptothecin, trifluoroacetate By the method of the procedure of Example 1.1.c, the conjugate from Example 2.3.a is linked with $N^\alpha$-(tert-butoxycarbonyl)-$N^\epsilon$-(fluorenyl-9-methoxycarbonyl)-lysine and subsequently deblocked at the α-amino function by the action of trifluoroacetic acid. Yield: 52% over 2 steps.

2.3.c) 20(S)-10,11-Methylenedioxy-20-O-{$N^\alpha$-[O-(3-O-carboxymethyl-β-L-fucopyranosyl)-4-hydroxy-phenylamino-thiocarbonyl]-$N^\epsilon$-[fluorenyl-9-methoxycarbonyl]-lysyl-alanyl}-camptothecin By the method of Example 1.1, the compound from Example 2.3.b is reacted with 1.2 equivalents of the carbohydrate derivative from Example I.2. The crude product is purified by stirring with water and subsequent precipitation from dichloromethanelmethanol using ether. Yield: 88% [TLC: dichloromethane/methanol/17% strength ammonia 15:4:0.5 $R_f$=0.27]

2.3) 20(S)-10,11-Methylenedioxy-20-O-{$N^\alpha$-[O-(3-O-carboxymethyl-β-L-fucopyranosyl)-4-hydroxy-phenylamino-thiocarbonyl]-lysyl-alanyl}-camptothecin, hydrochloride The conjugate 2.3.c is deblocked using piperidine in DMF. After 20 min, the mixture is concentrated and the residue is digested twice with dichloromethane. The product is filtered off with suction, washed again with ether and then lyophilized from dioxane/water. The lyophilizate is subsequently taken up in dioxane/water, admixed with 1 equivalent of a 0.1 N HCl solution and once more lyophilized. Yield: quantitative [TLC: acetonitrile/water/glacial acetic acid 5:1:0.2 $R_f$=0.26][FAB-MS: m/z=947=M+H]

Example 2.4

20(S)-10,11-Methylenedioxy-20-O-{$N^\alpha$-[O-(3-O-methyl-β-L-fucopyranosyl)-4-hydroxy-phenylamino-thiocarbonyl]-lysyl-leucyl}-camptothecin, hydrochloride

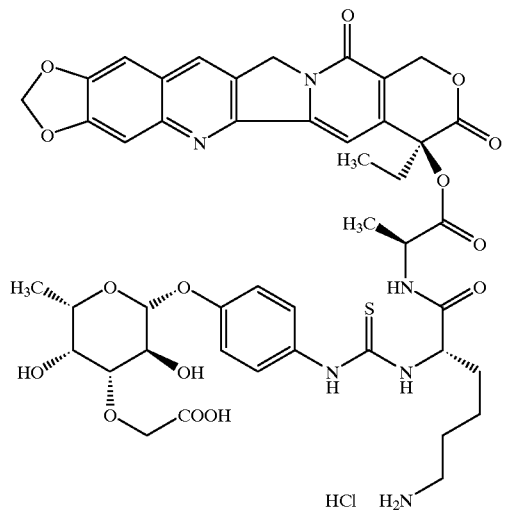

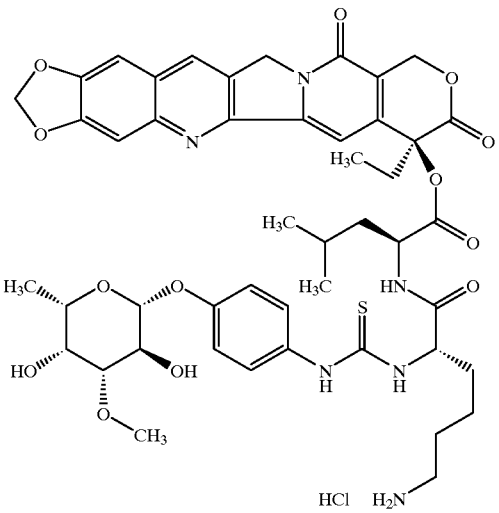

2.4.a) 20(S)-10,11-Methylenedioxy-20-O-leucyl-camptothecin, trifluoroacetate

By the method of Example 2.1.b and starting from 20(S)-10,11-methylenedioxy-camptothecin (Example 2.2.a), the target compound is prepared using N-(tert-butoxycarbonyl)-leucine-N-carboxylic anhydride.

2.4.b) 20(S)-10,11-Methylenedioxy-20-O-{N$^\epsilon$-[fluorenyl-9-methoxycarbonyl]-lysyl-leucyl}-camptothecin, trifluoroacetate By the method of the procedure of Example 1.1.c, the conjugate from Example 2.4.a is linked with N$^\alpha$-(tert-butoxycarbonyl)-N$^\epsilon$-(fluorenyl-9-methoxycarbonyl)-lysine and subsequently deblocked at the α-amino function by the action of trifluoroacetic acid. Yield: 69% over 2 steps.

2.4.c) 20(S)-10,11-Methylenedioxy-20-O-(N$^\alpha$-[O-(3-O-methyl-β-L-fucopyranosyl)-4-hydroxy-phenylamino-thiocarbonyl]-N$^\epsilon$-[fluorenyl-9-methoxycarbonyl]-lysyl-leucyl}-camptothecin By the method of Example 1.1, the compound from Example 2.4.b is reacted with 1.2 equivalents of the carbohydrate derivative from Example I.1. The crude product is purified by precipitation from dichloromethane/methanol using ether. Yield: 95% [TLC: acetonitrile/water 20:1 $R_f$=0.48].

2.4) 20(S)-10,11-Methylenedioxy-20-O-{N$^\alpha$-[O-(3-O-methyl-β-L-fucopyranosyl)-4-hydroxy-phenylamino-thiocarbonyl]-lysyl-leucyl}-camptothecin, hydrochloride.

The conjugate 2.4.c is deblocked using piperidine in DMF. After 20 nin, the mixture is concentrated and distilled twice, in each case after the addition of dichloromethane. The product is precipitated from dichloromethanelmethanol using ether. It is subsequently taken up in water, admixed with 1 equivalent of 0.1 N HCl solution and lyophilized. Yield: 75% [TLC: acetonitrile/water/glacial acetic acid 5:1:0.2 $R_f$=0.47].

Example 3.1

20(S)-9-Amino-20-O-{N$^\alpha$,N$^\epsilon$-bis-[O-(3-O-methyl-β-L-fucopyranosyl)4-hydroxy-phenylamino-thiocarbonyl]-lysyl-alanyl}-camptothecin

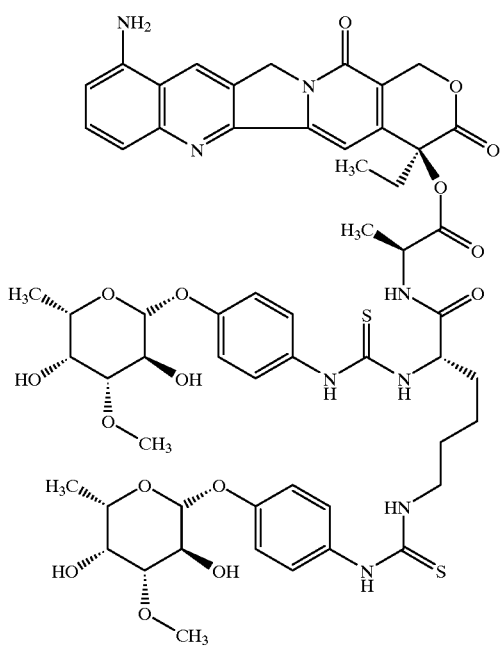

3.1.a) 20(S)-9-Nitro-camptothecin

This derivative is prepared by the procedure of Wani et al. (J.Med.Chem. 29 (1986), 2358).

3.1.b) 20(S)-9-Nitro-20-O-alanyl-camptothecin, trifluoroacetate 516 mg (1.31 mmol) of the compound from Example 3.1.a in 55 ml of absolute dimethylformamide are admixed with stirring with 846 mg (3.9 mmol) of N-(tert-butoxycarbonyl)-alanine-N-carboxylic anhydride and 55 mg of 4-(N,N-dimethylamino)-pyridine. After 4 h, the mixture is concentrated under reduced pressure and the residue is chromatographed over silica gel using dichloromethane/ethyl acetate 2:1. The recovered starting material is once more reacted under the same conditions, giving the protected intermediate in a yield of 54%. [TLC: dichloromethane/methanol 95:5 $R_f$=0.5]. The intermediate is taken up in 40 ml of dichloromethane, and 4 ml of anhydrous trifluoroacetic acid are added at 0° C. After 15 min, the mixture is concentrated and the product is purified by trituration with ether. Yield: 80%.

3.1.c) 20(S)-9-Amino-20-O-alanyl-camptothecin, trifluoroacetate 320 mg (0.55 mmol) of the compound from 3.1.b are taken up in 30 ml of ethanol and hydrogenated over 10 mg of platinum dioxide for 15 min. The catalyst is filtered off, the solution is concentrated and the product is, after precipitation from dichloromethane using methanol, employed for the next step.

3.1.d) 20(S)-9-Amino-20-O-(lysyl-alanyl)-camptothecin, di-trifluoroacetate 31 mg (0.09 mmol) of N,N-di-(tert-butoxycarbonyl)-lysine in 5 ml of dimethylformamide are preactivated with 15 mg (0.135 mmol) of N-hydroxy-succinimide and 22 mg (0.11 mmol) of dicyclohexyl-carbodiimide for 2 h. Compound 3.1.c (60 mg, 0.09 mmol) and 31 μl of ethyl-diisopropylamine are subsequently added, and the batch is stirred at room temperature for a further 16 h. Concentration under reduced pressure and purification by flash chromatography [toluene/ethanol 8:1] gives the intermediate in a yield of 47%. [TLC: dichloromethane/methanol 9:1 $R_f$=0.31]. 30 mg (0.039 mmol) in dichloromethane (10 ml) are admixed with anhydrous trifluoroacetic acid (2 ml), and the resulting solution is stirred at room temperature for 30 min. The mixture is concentrated and the product is then precipitated from dichloromethane/methanol using ether (20 mg, 57%). [TLC: acetonitrile/water/glacial acetic acid 10:5:3 $R_f$=0.44].

3.1) 20(S)-9-Amino-20-O-{N$^\alpha$,N$^\epsilon$-bis-[O-(3-O-methyl-β-L-fucopyranosyl)-4-hydroxy-phenylamino-thiocarbonyl]-lysyl-alanyl}-camptothecin By the method of Example 1.1, the glycoconjugate is prepared from the compounds from 3.1.d and I.1. Yield: 58% [TLC: acetonitrile/water/glacial acetic acid 5:1:0.2 $R_f$=0.6].

Example 4.1

20(S)-7-{N<sup>α</sup>,N<sup>ε</sup>-bis-[O-(3-O-Methyl-β-L-fucopyranosyl)-4-hydroxy-phenylamino-thiocarbonylmino-thiocarbonyl]-lysyl-alanyloxymethyl}-20-O-{N<sup>α</sup>,N<sup>ε</sup>-bis-[O-(3-O-methyl-β-L-fucopyranosyl)-4-hydroxy-phenylamino-thiocarbonyl]-lysyl-alanyl}-camptothecin

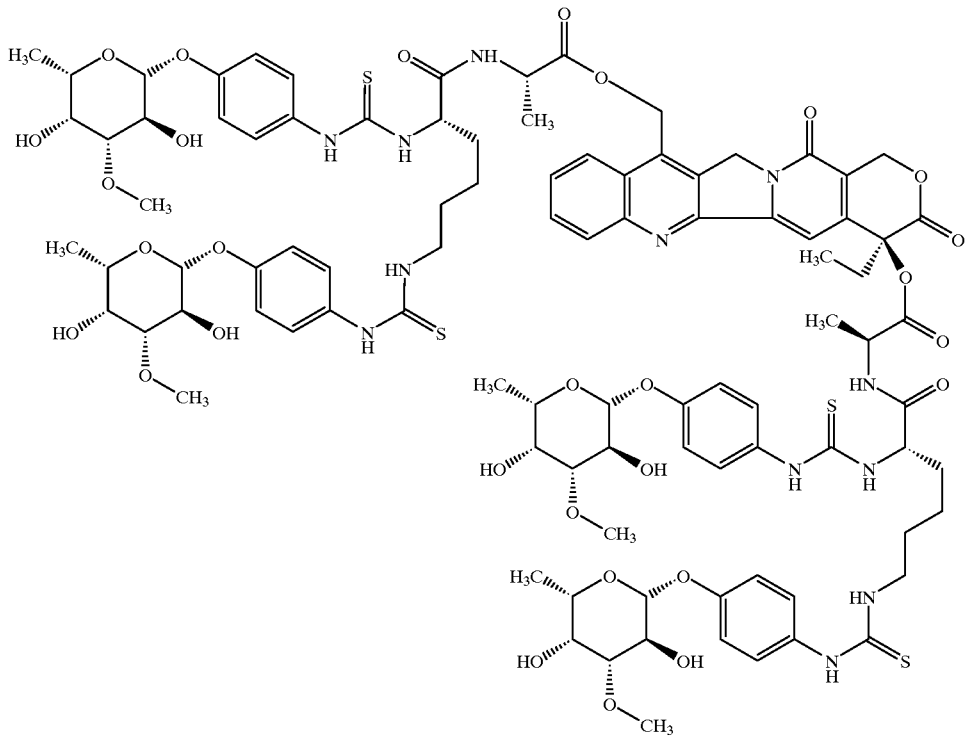

4.1.a) 20(S)-7-Hydroxymethyl-camptothecin

This compound is prepared according to the procedure of Miyasaka et al. (Chem. Pharm. Bull. 39 (1991) 2574).

4.1.b) 20(S)-7-(Alanyloxymethyl)-20-O-alanyl-camptothecin, di-trifluoroacetate 1 g (2.64 mmol) of 20(S)-7-hydroxymethyl-camptothecin is dissolved in 100 ml of DMF and then admixed with 100 mg of 4-N,N-dimethylaminopyridine and 1.5 equivalents of N-(tert-butoxycarbonyl)-L-alanine-N-carboxylic anhydride, and the suspension is stirred at room temperature for 16 h. To achieve complete double acylation, another 100 mg of 4-N,N-dimethylaminopyridine and 1.5 equivalents of N-(tert-butoxycarbonyl)-alanine-N-carboxylic anhydride are added, and the mixture is left at room temperature for a further 16 h. The mixture is concentrated and purified by flash chromatography using ethyl acetate/petroleum ether 1:1. The purified material is taken up in 30 ml of dichloromethane and, at 0° C., admixed with 5 ml of trifluoroacetic acid. The mixture is stirred for 30 min and then concentrated, and the amino-deblocked product is precipitated from dichloromethane/ether and subsequently lyophilized from dioxane/water. [TLC: acetonitrile/water/ glacial acetic acid 10:5:5 R<sub>f</sub>=0.17] [FAB-MS: m/z=777=M+H].

4.1) 20(S)7-{N<sup>α</sup>,N<sup>ε</sup>-bis-[O-(3-O-methyl-β-L-fucopyranosyl)-4-hydroxyphenylamino-thiocarbonyl]-lysyl-alanyloxymethyl}-20-O-{N<sup>α</sup>,N<sup>ε</sup>-bis-[O-(3-O-methyl-β-L-fucopyranosyl)4-hydroxy-phenylamino-thiocarbonyl]-lysyl-alanyl}-camptothecin By the methods of Examples 1.1.c, 1.1.d and 1.1, the conjugate is prepared from the compound of Example 4.1.b, but using, in all steps, double the amount of the reactants in question. [TLC: acetonitrile/water 10:1 R<sub>f</sub>=0.2] [MALDI-MS: m/z=2047=M(+3)+Na].

Example 5.1

20(S)-7-[4-(Methylpiperazino)methy]-10,11-(ethylenedioxy)-20-O-{N<sup>α</sup>-[O-(3-O-methyl-β-L-fucopyranosyl)4-hydroxy-phenylamino-thiocarbonyl-lysyl-leucyl}-camptothecin, hydrochloride

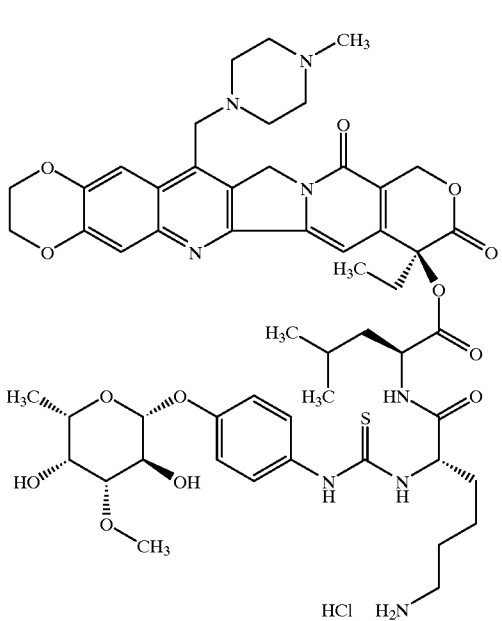

5.1.a) 20(S)-7-[(Methylpiperazino)methyl]-10,11-(ethylenedioxy)-camptothecin, trifluoroacetate This derivative is prepared according to the procedure of Luzzio et al. (J.Med.Chem. 38 (1995), 396).

5.1.b) 20(S)-7-[4-(Methylpiperazino)methyl]-10,11-(ethylenedioxy)-20-O-leucyl-camptothecin, tri-trifluoroacetate By the method of Example 2.1.b, the target compound is prepared starting from the compound from Example 5.1.a) and using N-(tert-butoxycarbonyl)-leucine-N-carboxylic anhydride (10 equivalents). The Boc-protected intermediate is purified by flash chromatography (dichloromethane/methanol/17% strength ammonia 15:1:0.1]. Yield: 62% over 2 steps [ESI-MS: m/z=632=M+H; m/z=654=M+Na].

5.1.c) 20(S)-7-[4-(Methylpiperazino)methyl]-10,11-(ethylenedioxy)-20-O-{$N^\epsilon$-[fluorenyl-9-methoxycarbonyl]-lysyl-leucyl}-camptothecin, tri-trifluoroacetate By the method of the procedure of Example 1.1.c, the conjugate from Example 5.1.b is linked with $N^\alpha$-(tert-butoxycarbonyl)-$N^\epsilon$-(fluorenyl-9-methoxycarbonyl)-lysine and subsequently deblocked at the α-amino function by action of trifluoroacetic acid. The Boc-protected intermediate is purified by flash chromatography [dichloromethane/methanol 10:1]. Yield: 53% over 2 steps. [TLC: acetonitrile/water/glacial acetic acid 5:1:0.2 $R_f$=0.13] [FAB-MS: m/z=982=M+H].

5.1.d) 20(S)-7-[4-(Methylpiperazino)methyl]-10,11-(ethylenedioxy)-20-O-{$N^\alpha$-[O-(3-O-methyl-β-L-fucopyranosyl)-4-hydroxy-phenylamino-thiocarbonyl]-$N^\epsilon$-[fluorenyl-9-methoxycarbonyl]-lysyl-leucyl}-camptothecin By the method of Example 1.1, the compound from Example 5.1.c is reacted with 1.2 equivalents of the carbohydrate derivative from Example I.1. The crude product is purified by precipitation from methanol using ether. Yield: 83% [TLC: acetonitrile/water/glacial acetic acid 5:1:0.2 $R_f$=0.21].

5.1) 20(S)-7-[4-(Methylpiperazino)methyl]-10,11-(ethylenedioxy)-20-O-{$N^\alpha$-[O-(3-O-methyl-β-L-fucopyranosyl)-4-hydroxy-phenylamino-thiocarbonyl]-lysyl-leucyl}-amptothecin, hydrochloride The conjugate 5.1.d is deblocked using piperidine in DMF. After 20 min, the mixture is concentrated and the residue is distilled twice after addition of dichloromethane.

The product is precipitated from dichloromethane/methanol using ether. It is subsequently taken up in water, admixed with 1 equivalent of a 0.1 N HCl solution and lyophilized. Yield: 95% [TLC: acetonitrile/water/glacial acetic acid 10:3:1.5 $R_f$=0.15] [FAB-MS: m/z=1071=M+H].

Example 6.1

7-Ethyl-10-hydroxy-20-O-{$N^\alpha$-[O-methyl-β-L-fucopyranosyl)-4-hydroxy-phenylamino-thiocarbonyl]-lysyl-valyl}-camptothecin, hydrochloride

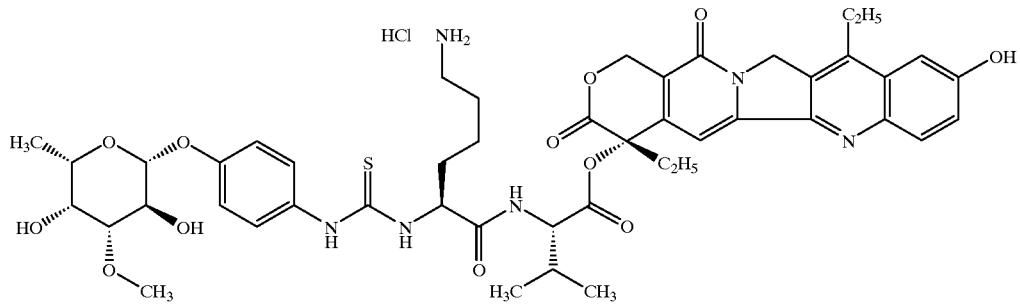

6.1.a) 20-O-[N-(tert-Butoxycarbonyl)-valyl]-7-ethyl-10-hydroxy-camptothecin

Using the process described in 1.1.a, the compound is prepared from 392.4 mg (1.0 mmol) of 20(S)-7-ethyl-10-hydroxy-camptothecin (S. Sawada et al., Chem. Pharm. Bull. 39 (1991) 3183–3188) and a total of 2.43 g (10.0) of N-(tert-butoxycarbonyl)-valine-N-carboxylic anhydride over a period of 6 days. Flash chromatography [petroleum ether/ethyl acetate 5:1→2:1→1:1] gives 353 mg (45%) of light-yellow crystals [TLCL acetonitrile/ethyl acetate 1:1 $R_f$=0.63; m.p.=95–97° C.].

6.1.b) 7-Ethyl-10-hydroxy-20-O-valyl-camptothecin, trifluoroacetate

From compound 6.1.a (340 mg, 0.43 mmol), the N-tert-butoxycarbonyl) group is cleaved off as described under 1.1.b. This gives 255 mg (98%) of yellow crystals [TLC (acetonitrile/ethyl acetate 1:1): $R_f$=0.04: m.p.=189° C. (Decomp.)].

6.1.c) 20-O-[$N^\alpha$-(tert-Butoxycarbonyl)-$N^\epsilon$-(fluorenyl-9-methoxycarbonyl)-lysyl-valyl]-7-ethyl-10-hydroxy-camptothecin By the method of 1.1.c, 562.3 mg (1.2 mmol) of $N^\alpha$-(tert-butoxycarbonyl)-$N^\epsilon$-(fluorenyl-9-methoxycarbonyl)-lysine are reacted with compound 6.1.b (242.2 mg, 0.4 mmol). Concentration under reduced pressure and purification by flash chromatography [petroleum ether/ethyl acetate 5:1→3:1→1:1] gives yellow crystals. Yield: 251 mg (67%) [TLC (acetonitrile/ethyl acetate 1:1): $R_f$=0.68; m.p.=163° C. (Decomp.)].

6.1.d) 7-Ethyl-2-O-[$N^\epsilon$-(fluorenyl-9-methoxycarbonyl)-lysyl-valyl]-10-hydroxy-camptothecin, trifluoroacetate The above compound (244.9 mg, 0.26 mmol) is deprotected as described, using trifluoroacetic acid in dichloromethane. This gives 115 mg (46%) of yellow crystals [TLC (acetonitrile/ethyl acetate 1:1): $R_f$=0.05; m.p.=196° C. (Decomp.)]

6.1.e) 20(S)-7-Ethyl -10-hydroxy-20-O-{$N^\alpha$-[O-methyl-β-L-fucopyranosyl)-4-hydroxy-phenylamino-thiocarbonyl]-$N^\epsilon$-[fluorenyl-9-methoxycarbonyl]-lysyl-valyl}-camptothecin By the method of Example 1.1, the compound from Example 6.1.d is reacted with equivalents of the carbohydrate derivative from Example 1.1, and the product is purified by flash chromatography [petroleum ether/ethyl acetate 1:1→2:3→1:2]. Beige crystals are obtained in a yield of 36% [TLC (acetonitrile/ethyl acetate 1:1): $R_f$=0.55].

6.1) 20(S)-7-Ethyl-10-hydroxy-20-O-{$N^\alpha$-[O-(3-O-methyl-β-L-fucopyranosyl)-4-hydroxy-phenylamino-thiocarbonyl]-lysyl-valyl}-camptothecin, hydrochloride.

The conjugate 6.1.e is deblocked using piperidine in DMF. After 2 h, the mixture is concentrated and the residue is precipitated twice from dichloromethane/methanol 1:1 using diethyl ether. The precipitate is then taken up in water, admixed with 1 equivalent of a 0.01 N HCl solution and lyophilized.

What is claimed is:

1. Compounds of the general formula (I)

A—Cp—B  (I)

in which

Cp represents a group of the formulae

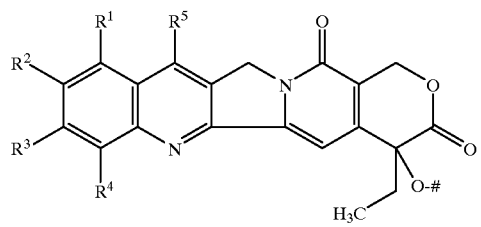

1)

in which $R^1$, $R^2$, $R^3$ and $R^4$ independently of one another may represent hydrogen, alkyl having up to 3 carbon atoms, halogen, amino, hydroxyl or nitro or $R^2$ and $R^3$ together represent a group of the formula

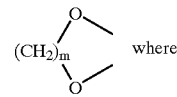

m may have the values 1 or 2 and $R^5$ represents —$CH_2$—O—*, —$CH_2$—NH*,

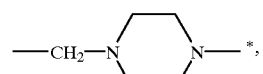

or represents

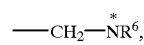

in which $R^6$ represents arylmethyl or hetarylmethyl, $R^1$–$R^5$ not all being hydrogen

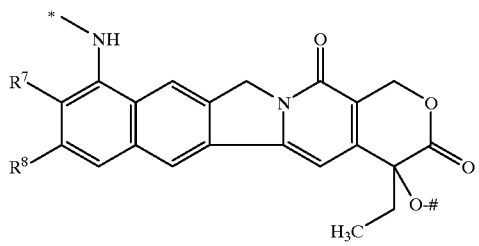

2)

in which $R^7$ and $R^8$ are as defined for $R^2$ and $R^3$ and may be identical or different to these,

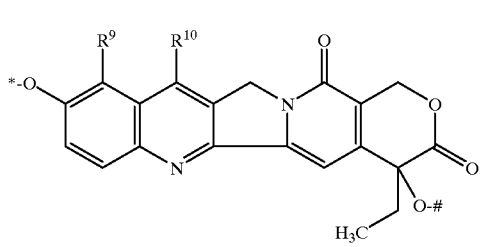

3)

in which $R^9$ represents hydrogen or —$CH_2$—$N(CH_3)_2$ and $R^{10}$ represents hydrogen or ethyl, or

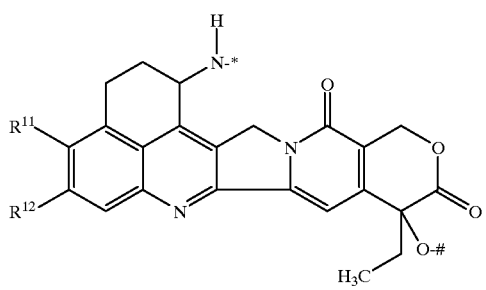

4)

in which $R^{11}$ and $R^{12}$ are as defined for $R^2$ and $R^3$ and may be identical or different to these, or

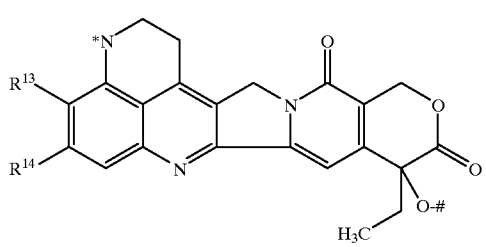

5)

in which $R^{13}$ and $R^{14}$ are as defined for $R^2$ and $R^3$ and may be identical or different to these, where Cp is attached to A on the positions labelled #
and attached to B on the positions labelled *,
A represents a radical of the formula

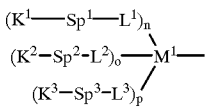

where $1 \leq (n+o+p) \leq 3$,
B represents hydrogen or a radical of the formula

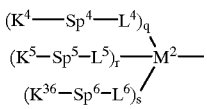

where $0 \leq (q+r+s) \leq 3$, in which
$M^1$ and $M^2$ independently of one another each represent a bridge grouping whose main chain includes up to 21 atoms in linear order,
$L^1$, $L^2$, $L^3$, $L^4$, $L^5$ and $L^6$ independently of one another each represent linker groupings,
$Sp^1$, $Sp^2$, $Sp^3$, $Sp^4$, $Sp^5$ and $Sp6$ independently of one another each represent arylene having up to 10 carbon atoms or represent alkylene having up to 8 carbon atoms which are in each case optionally substituted, and
$K^1$, $K^2$, $K^3$, $K^4$, $K^5$ and $K^6$ independently of one another each represent a radical of the formula (II)

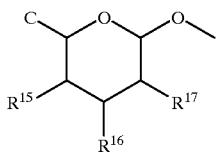

in which
C represents methyl, hydroxymethyl, alkoxymethyl having up to 6 carbon atoms, acyloxymethyl having up to 6 carbon atoms or a radical of the formula $—CH_2—D$
in which
D represents a radical of the formula (II),
$R^{15}$, $R^{16}$ and $R^{17}$ independently of one another each represent hydrogen, hydroxyl, optionally hydroxyl-substituted alkoxy having up to 6 carbon atoms, amino which is optionally substituted by alkyl or acyl having up to 6 carbon atoms, halogen, sulphate or a group of the formulae

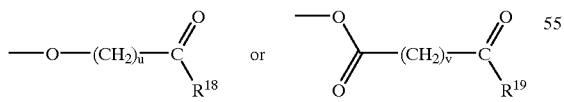

in which
$R^{18}$ and $R^{19}$ independently of one another each represent hydroxyl or alkoxy having up to 6 carbon atoms or represent amino which is optionally substituted by alkyl having up to 6 carbon atoms, and
u and v independently of one another may each have the values 0, 1, 2, 3 or 4, in particular the values 1, 2, 3 or 4, or
$R^{15}$, $R^{16}$ and $R^{17}$ independently of one another each represent a radical of the formula (II)
or
two of the radicals $R^{15}$, $R^{16}$, $R^{17}$ together represent an epoxy group, or compounds of the formula;

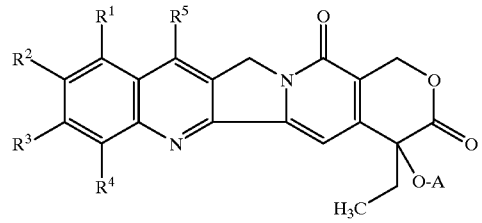

in which
$R^1$, $R^2$, $R^3$, $R^4$, and A are as defined above; and
$R^5$ represents H, $—CH_2CH_3$,

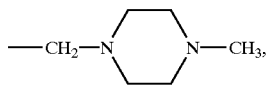

or represents $—CH_2—N(CH_2CH_3)R^6$,
in which $R^6$ represents arylmethyl or hetarylmethyl,
and their isomers, isomer mixtures and salts.

2. Compounds of the general formula (I) according to claim 1, in which $K^1$, $K^2$, $K^3$, $K^4$, $K^5$ and $K^6$ independently of one another may each represent a radical of the formula (II) where
C represents methyl, hydroxymethyl, methoxymethyl or acetoxymethyl,
$R^{15}$ represents hydrogen, hydroxyl, methoxy or a group of the formula

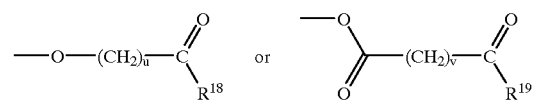

in which
u and v independently of one another may each have the values 1 or 2 and
$R^{18}$ and $R^{19}$ independently of one another each represent hydroxyl or alkoxy having up to 4 carbon atoms,
or
$R^{15}$ represents a radical of the formula (II),
$R^{16}$ represents hydrogen, hydroxyl, halogen, alkoxy having up to 4 carbon atoms, sulphate or a group of the formula

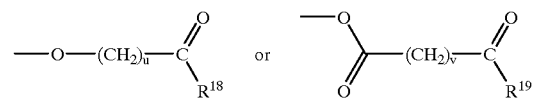

in which
u and v independently of one another may each have the values 1 or 2 and
$R^{18}$ and $R^{19}$ independently of one another each represent hydroxyl or alkoxy having up to 4 carbon atoms or represent amino which is optionally substituted by alkyl having up to 4 carbon atoms, $R^{17}$ represents hydroxyl, alkoxy having up to 4 carbon atoms which is optionally substituted by hydroxyl, amino which is optionally substituted by alkyl or acyl having up to 4 carbon atoms, or a group of the formula

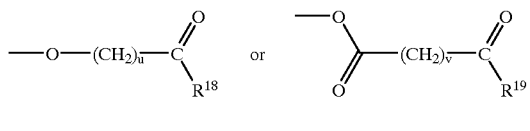

in which
u and v independently of one another may each have the values 1 or 2 and
$R^{18}$ and $R^{19}$ independently of one another each represent hydroxyl or alkoxy having up to 4 carbon atoms, or in which
$R^{15}$ and $R^{16}$ together represent an epoxy group,
and their isomers, isomer mixtures and salts.

3. Compounds of the general formula (I) according to claim 1 in which $Sp^1$, $Sp^2$, $Sp^3$, $Sp^4$, $Sp^5$ and $Sp^6$ independently of one another may each represent arylene having up to 10 carbon atoms which is attached to in each case one group $K^1$, $K^2$, $K^3$, $K^4$, $K^5$ or $K^6$ and $L^1$, $L^2$, $L^3$, $L^4$, $L^5$ or $L^6$ and which is optionally also mono- or polysubstituted by hydroxyl, carboxyl, carboxyalkyl having up to 4 carbon atoms, nitro, cyano, halogen, alkyl having up to 4 carbon atoms, halogenoalkyl having up to 4 carbon atoms or by alkoxy having up to 4 carbon atoms, and their isomers, isomer mixtures and salts.

4. Compounds of the general formula (I) according to claim 1 in which
$L^1$, $L^2$, $L^3$, $L^4$, $L^5$ and $L^6$ independently of one another each represent

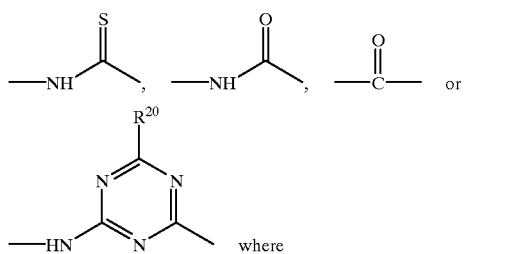

$R^{20}$ represents chlorine or represents hydroxyalkylamino having up to 6 carbon atoms,
and their isomers, isomer mixtures and salts.

5. Compounds of the general formula (I) according to claim 1, in which u and v independently of one another have the values 1, 2, 3, or 4.

6. Compounds of the general formula (I) according to claim 1 in which $M^1$ and $M^2$ independently of one another may each represent a peptide which is attached to $L^1$, $L^2$, $L^3$, $L^4$, $L^5$ and/or $L^6$ via an amino function, is attached to Cp via an acyl function and whose amino acid building blocks may optionally carry protective groups, and their isomers, isomer mixtures and salts.

7. Compounds according to claim 5, characterized in that $M_1$ and/or $M_2$ represent a mono-, di- or tripeptide.

8. Compounds according to claim 5, characterized in that the peptide comprises amino acid building blocks selected from the group consisting of glycyl, alanyl, valyl, leucyl, lysyl, seryl, glutamyl, threonyl, asparagyl, isoleucyl, diaminopropionyl, diaminobutyryl, arginyl, histidyl and/or ornithyl which optionally carry protective groups.

9. A process for preparing a compound of the formula (I) according to claim 1, comprising:
a) reacting a compound of the formula (III):

$$H_B\text{—}C_P\text{—}H_A$$

in which $C_P$ is as defined in claim 1 and $H_A$ and $H_B$ represent hydrogen atoms located on the positions labelled # and *, respectively, with an activated carboxyl component:

$$M^1a$$

in which $M^1$ is as defined in claim 1, and optionally carries protective groups, said reacting being in a suitable solvent, optionally in the presence of a base, and optionally after replacing $H_B$ by a protective group;
b) optionally selectively removing one or more protective groups of $M^1$;
c) reacting the product of a) or b) with a compound of the general formula (IV):

$$K^1\text{—}Sp^1\text{—}L^1a$$

in which $K^1$ and $Sp^1$ are each as defined in claim 1 and $L^1a$ represents a reactive precursor of the group $L^1$;
d) optionally selectively removing one or more protective groups;
e) optionally introducing groups $K^2$—$Sp^2$—$L^2$— and $K^3$—$Sp^3$—$L^3$— in a manner analogous to c); and
f) if a carbohydrate component is to be attached to the position labelled *, optionally selectively removing a protective group which replaces $H_B$, and optionally introducing a radical $M^2$, $K^4$—$Sp^4$—$L^4$—, $K^5$—$Sp^5$—$L^5$— and/or $K^6$—$Sp^6$—$L^6$— in a manner analogous to a) to e) above; or
g) if M1 and/or M2 are a peptide, then:
i) introducing a first amino acid radical in the form of a corresponding carboxyl component, which, optionally, carries one or more protective groups;
ii) optionally removing one or more of said protective groups;
iii) attaching an amino radical, which, optionally, carries one or more protective groups;
iv) optionally removing one or more of said protective groups;
v) introducing said radicals of the formulae $K^1$—$Sp^1$—$L^1$—, $K^2$—$Sp^2$—$L^2$—, $K^3$—$Sp^3$—$L^3$—, $K^4$—$Sp^4$—$L^4$—, $K^5$—$Sp^5$—$L^5$— and/or $K^6$—$Sp^6$—$L^6$—;
vi) optionally removing one or more protective groups;
h) optionally separating stereoisomers of said compound of formula (I); and
i) optionally converting said compound of formula (I) into its salt.

10. A pharmaceutical composition comprising at least one compound of the formula (I) according to claim 1 and a non-toxic, inert pharmaceutically suitable excipient.

11. A method of treating a cancer in a patient comprising administering to said patient an effective amount therefor of at least one compound of the formula (I) according to claim 1.

* * * * *